US007935309B2

(12) United States Patent
McGimpsey et al.

(10) Patent No.: US 7,935,309 B2
(45) Date of Patent: May 3, 2011

(54) MULTI-TRANSDUCTION MECHANISM BASED MICROFLUIDIC ANALYTE SENSORS

(75) Inventors: W. Grant McGimpsey, Boylston, MA (US); Christopher R. Lambert, Hudson, MA (US); John S. Benco, Holliston, MA (US); Venkat R. Thalladi, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 385 days.

(21) Appl. No.: 11/404,319

(22) Filed: Apr. 14, 2006

(65) Prior Publication Data

US 2007/0042450 A1   Feb. 22, 2007

Related U.S. Application Data

(60) Provisional application No. 60/671,857, filed on Apr. 15, 2005.

(51) Int. Cl.
*G01N 21/62* (2006.01)
*G01N 21/64* (2006.01)
*G01N 27/00* (2006.01)
*G01N 33/00* (2006.01)
*G01N 33/20* (2006.01)
*G01N 33/48* (2006.01)
*G01N 33/50* (2006.01)
*G01N 33/53* (2006.01)
*G01N 33/533* (2006.01)

(52) U.S. Cl. ... 422/82.08; 422/50; 422/68.1; 422/82.01; 422/82.02; 422/82.03; 422/82.06; 422/102; 422/103; 422/104; 435/287.2; 436/73; 507/136

(58) Field of Classification Search .................. None
See application file for complete search history.

(56) References Cited

U.S. PATENT DOCUMENTS

| | | | | | |
|---|---|---|---|---|---|
| 4,655,880 | A | * | 4/1987 | Liu | 205/777.5 |
| 5,034,189 | A | * | 7/1991 | Cox et al. | 422/52 |
| 5,591,581 | A | * | 1/1997 | Massey et al. | 435/6 |
| 5,959,619 | A | * | 9/1999 | Kameyama et al. | 345/204 |
| 6,197,595 | B1 | * | 3/2001 | Anderson et al. | 436/180 |
| 6,573,109 | B1 | | 6/2003 | Cornell et al. | |
| 6,660,526 | B2 | * | 12/2003 | Benco et al. | 436/79 |
| 2002/0009810 | A1 | * | 1/2002 | O'Connor et al. | 436/518 |

FOREIGN PATENT DOCUMENTS

WO    WO-98/58246 A2    12/1998

OTHER PUBLICATIONS

Baudenbacher, F. et al., "The Nanophysiometer: Biomems for High Bandwidth Detection of Cellular Activity in Subnanoliter Volumes," *Proceedings of the Second Joint EMBS/BMES Conference*, pp. 1690-1691 (2002).
Du, Hui et al., "Hybridization-Based Unquenching of DNA Hairpins on Au Surfaces: Prototypical 'Molecular Beacon' Biosensors," *J. Am. Chem. Soc.*, vol. 125:4012-4013 (2003).
International Search Report for Application No. PCT/US2006/014079, dated Nov. 17, 2006.

* cited by examiner

*Primary Examiner* — Unsu Jung
(74) *Attorney, Agent, or Firm* — Nelson Mullins Riley & Scarborough LLP; Anthony A. Laurentano; Pankaj N. Desai

(57) ABSTRACT

In various aspects are provided a microfluidic and/or nanofluidic sensor that can provide an indication of the reliability of its measurement of the presence of an analyte in a sample under investigation, an analyte concentration in the sample under investigation, or both. The provided sensors, microfluidic devices, and methods of analyte detection, utilize two transduction mechanisms from the same molecule to determine analyte presence, analyte concentration, or both. An analyte sensing molecule is used that can provide both an optical signal and electrochemical signal when an analyte is recognized by an analyte binding portion of the sensing molecule.

16 Claims, 12 Drawing Sheets

MULTI-TRANSDUCTION MECHANISM BASED MICROFLUIDIC ANALYTE SENSORS

CROSS-REFERENCE TO RELATED APPLICATIONS

The present application claims the benefit of and priority to copending U.S. provisional application No. 60/671,857 filed Apr. 15, 2005, the entire disclosure of which is herein incorporated by reference.

INTRODUCTION

The field of microfluidics has a number of emerging applications in analytical chemistry and chemical processing. One area of application is in the field of point-of-care (POC) analyte sensors, e.g., blood electrolyte sensors. Traditionally, most hospital electrolyte tests are performed in large, multiple-analyte analyzers in a chemistry or medical laboratory. Vials of blood are drawn from the patient for sampling, and hours, and even days, may pass before the caregiver receives the results. Various technologies have been proposed to provide a POC analyte sensor, but ultimately, reliability of sensor data is important, if not critical, if decisions are to be made without the use of traditional laboratory tests.

For example, electrochemical sensors using ion-selective electrode technology have been tried as POC electrolyte sensors. One example of an ion-selective electrode POC sensor is the i-STAT system, available from the i-STAT Corporation. The i-STAT system utilizes a blood sample that is drawn from the patient and injected into a cartridge including microfabricated, ion-selective electrodes, a calibration fluid pouch, and plastic structures for directing fluid flow and storing waste. The fluid pouch, containing known concentrations of the analytes, is punctured at the onset of a test, and the calibration fluid passes over the sensors, allowing a one-point calibration. The fluid is then flushed into the waste container and the blood sample is drawn in for testing.

Interferants, especially in the measurement of analyte concentrations in biological samples, can render unreliable analyte concentration measurements. For example, many glucose meters intended for home use are susceptible to interference from redox active materials such as vitamin C. The list of potential interferants in analyte concentration measurements of biological samples is long, and includes ions, biochemicals, proteins, cells and cellular debris. Accordingly, the reliability of concentration measurements made using traditional microfluidic sensors can be in question. Moreover, traditional microfluidic sensors do not provide, and often cannot provide, an indication of the whether of their individual measurements are in error. As a result, physicians cannot necessarily rely solely on the measurement provided by a traditional microfluidic sensor; this is a serious drawback for use of microfluidic sensors as POC sensors as a replacement for more traditional laboratory analysis of, e.g., blood samples.

SUMMARY OF THE INVENTION

The present invention, in various aspects, provides a microfluidic and/or nanofluidic sensor that can provide an indication of the reliability of its measurement of the presence of an analyte in a sample under investigation, an analyte concentration in the sample under investigation, or both.

The terms "microfluidic sensor" and "microfluidic device" typically refer, respectively, to a sensor or device that can operate with sample volumes on the microliter scale. Microfluidic may also refer to the dimensions of the device. A 100×100×100 µm cube is one nanolitre, therefore a channel 10 µm×10 µm×1 cm is also 1 nanoliter. As will become apparent from the following disclosure of the present invention, the present teachings can also provide sensors and devices that can operate with sample volumes on the nanoliter scale. It is to be understood that although the sensors of the present invention are often referred to as "microfluidic sensors" and the devices as "microfluidic devices" herein and in the claims, the phrase "microfluidic" as used in relation to the present invention includes embodiments capable of operation with nanoliter scale sample volumes. When referring to the prior art, however, the term "microfluidic" is not meant to imply that such prior art sensors or devices are capable of operation with nanoliter scale samples. Accordingly, the term "microfluidic" is used in describing the present invention instead of "microfluidic and/or nanofluidic" merely for the sake of conciseness in explanation of the present invention.

The present invention provides analyte sensors, microfluidic devices, and methods of analyte detection, that utilize two transduction mechanisms from the same molecule to determine analyte presence, analyte concentration, or both. The sensors, devices, and methods of the present invention utilize an analyte sensing molecule that can provide both an optical signal and electrochemical signal when an analyte is recognized by an analyte binding portion of the sensing molecule. The analyte sensing molecules comprise both an analyte binding portion and a fluorophore portion. Binding of an analyte to the analyte binding portion results in both an electrochemical signal and an optical signal by changing a fluorescence signal from the fluorophore (e.g., by turning on, turning off, increasing, decreasing, changing the wavelength of absorption or emission (thereby changing an wavelength excitation ratio or emission ratio, changing the lifetime of, etc, the fluorescence signal). The electrochemical signal can be detected by any of a number of electrochemical measurement techniques, including, but not limited to, capacitance, potentiometric, amperometric, coulombic, and/or AC analysis techniques. As a result, the binding of an analyte is transduced by two different mechanisms resulting in two signals (fluorescence and electrochemical) that each provide a separate concentration measurement for the analyte. A comparison of these two concentration measurements (e.g., a ratiometric comparison) provides a measure of the reliability of the measurement. In various embodiments, the comparison of the concentration determined from the fluorescence signal and that determined from the electrochemical signal is used to determine when an analyte sensor or microfluidic device of the present invention is in need of calibration or disposal.

In various aspects, the present invention provides an analyte sensor comprising a substrate having an electrically conductive material covering at least a portion of its surface and an analyte sensing molecule layer covering at least a portion of the electrically conductive material. The analyte sensing molecules comprising: (a) an analyte binding portion; (b) a fluorophore portion; and (c) a linker portion connecting the analyte sensing molecule to the electrically conductive material. In various embodiments, the analyte sensing molecule layer is a substantially monolayer thick film of the analyte sensing molecules.

In various embodiments, the analyte binding portion is directly attached to the electrically conductive material with a coupling group to facilitate, e.g., increasing sensor response time and sensitivity.

The present invention, in various embodiments, addresses the deficiencies of the prior art by providing analyte sensors, microfluidic devices, and methods of analyte detection, which can be utilized to analyze microfluidic sample volumes, i.e., sample volumes on the order of 1 to 1000 microliters, and, in various embodiments, sample volumes on the order of 1 to 1000 nanoliters. For example, analyte sensors, microfluidic devices, and methods of analyte detection of the present invention can be used in various embodiments to analyze microfluidic samples of water, biological fluids (such as, e.g., blood, plasma, serum, urine, saliva, sweat and tears), etc. Where the sample of interest, for example, is blood, the sample volumes only require a prick of the finger and not a blood draw to acquire a sample. Even smaller sample volumes may be obtained by suction techniques and electroactive techniques such as reverse iontophoresis. In various embodiments, the sensors, devices and methods of the present invention can be used, e.g., as for POC blood analyte (e.g., electrolyte, glucose, etc.) testing in hospitals, clinics, physicians' offices, or patients' homes. In various embodiments, the microfluidic devices of the present invention are reusable, instead of being a disposable cartridge, helping reduce, e.g., costs associated with the disposal of biomedical waste, which creates a more cost-effective device.

In various aspects, the present invention provides a microfluidic device comprising a substrate having an electrically conductive material covering at least a portion of its surface; an analyte sensor layer covering at least a portion of the electrically conductive material; a reference electrode in electrical contact with the analyte sensor layer; and a counter electrode in electrical contact with the analyte sensor layer. The analyte sensor layer comprising a substantially monolayer thick film of an analyte sensing molecule, the analyte sensing molecule comprising: (a) an analyte binding portion; (b) a fluorophore portion; and (c) a linker portion connecting the analyte sensing molecule to the electrically conductive material.

A microfluidic device of the present invention can be configured, e.g., as a hand-held device, a bench-top device, and as implantable sensors for physiological analytes, chemical hazards, biological hazards, etc. A microfluidic device of the present invention can be configured, e.g., to detect a single analyte, or multiple analytes, e.g., as a wide-spectrum physiological sensor.

In various aspects, the present invention provides methods for measuring an analyte concentration in a sample using two transduction mechanisms from the same sensor molecule species attached to an electrically conductive material on a substrate. In various embodiments, an optical determination and an electrochemical determination of analyte concentration are compared using a ratiometric method to determine the concentration of the analyte in the sample. In various embodiments, a ratiometric comparison of an optical determination and an electrochemical determination of analyte concentration are used to determine one or more of whether calibration is to be performed and one or more of the concentrations measurement are incorrect due, for example, to interferants.

A wide variety of sample types can be analyzed for the presence and/or concentration of one or more analytes using the analyte sensors, microfluidic devices and methods of the present invention including liquid and gaseous samples. Examples of samples amenable to analysis include, but are not limited to, biological fluids, water, and air.

In various embodiments, the analyte of interest in a sample is an ion and the analyte binding portion an ionophore for the ion. For example, an analyte binding portion can comprise an ionophore for, e.g., pH (i.e. $H^+$), $Na^+$, $K^+$, $Li^+$, $Cs^+$, $Ag^+$, $Ni^{+2}$, $Ca^{+2}$, $Cd^{+2}$, $Ba^{+2}$, $Mg^{+2}$, $Cu^{+2}$, $Pb^{+2}$, $Hg^{+2}$, $Fe^{+2}$, ammonium ions ($NH_4^+$), $Cl^-$, $Br^-$, $I^-$, $F^-$, $CN^-$, $OCl^-$, perchlorate ($ClO_4^-$), thiocyanate ($SCN^-$), sulphide ($S^-$), nitrate ($NO_3^-$), nitrite ($NO_2^-$), sulfate ($SO_3^-$), carbonate ($CO_3^-$), bicarbonate ($HCO_3^-$), and/or $S_2O_3^{-2}$ (thiosulfate).

One area of application of various embodiments of the analyte sensors, microfluidic devices, and methods of the present invention is in the measurement of blood analytes. The concentration of various ions and molecules in the blood can be of great importance for example healthcare field. For example, although lithium can be an effective treatment for manic-depressive disorders, the blood lithium level must be maintained over a narrow range; as a result, monitoring of lithium concentration in blood serum is important for these patients. Ammonium ion levels in the blood are used as an indirect measure of blood urea nitrogen (BUN); as BUN metabolizes to ammonium ions. BUN levels are, e.g., an important diagnostic of kidney function. Another important blood analyte is glucose. Monitoring of serum glucose levels is of particular importance for individuals with diabetes, as blood glucose levels need to be maintained in a specific range. For example, low serum glucose levels (e.g., below about 3.0 mmol/liter) can lead to hypoglycaemic shock, whereas high serum glucose levels can lead to hyperglycaemic shock.

An analyte of interest in environmental monitoring is nickel. Nickel is frequently used in catalytic processes and occurs in industrial effluents and hence may occur in ground water and as airborne pollution. Nickel at toxic levels, can cause acute pneumonitis, dermatitis, asthama, eczema, cancer of lungs and sinus, stomach aches, adverse effects on blood (increase red blood cells) and kidneys (increase protein in urine), and other disorders of respiratory system and central nervous system. Accordingly, monitoring of nickel in ground water, effluents, and the air, is another important application of various embodiments of the analyte sensors, microfluidic devices, and methods of the present invention.

In various embodiments, the analyte of interest can be indicative of exposure to a chemical and/or biological hazards, ("chem-bio hazards"), such as, for example, lead, aluminum, redox active pollutants, such as, e.g., methyl violgen based insecticides. Accordingly, another important application of various embodiments of the analyte sensors, microfluidic devices, and methods of the present invention is as chem-bio hazard monitors.

The foregoing and other aspects, embodiments, and features of the invention can be more fully understood from the following description in conjunction with the accompanying drawings. In the drawings like reference numerals generally refer to like features and structural elements throughout the various figures. The drawings are not necessarily to scale, emphasis instead being placed upon illustrating the principles of the invention.

BRIEF DESCRIPTION OF THE DRAWINGS

FIG. 11A schematically depicts the ionophore on a gold surface and FIG. 11B schematically depicts the ionophore modified to contain an anthracene fluorophore.

DETAILED DESCRIPTION OF THE INVENTION

Figure 1:
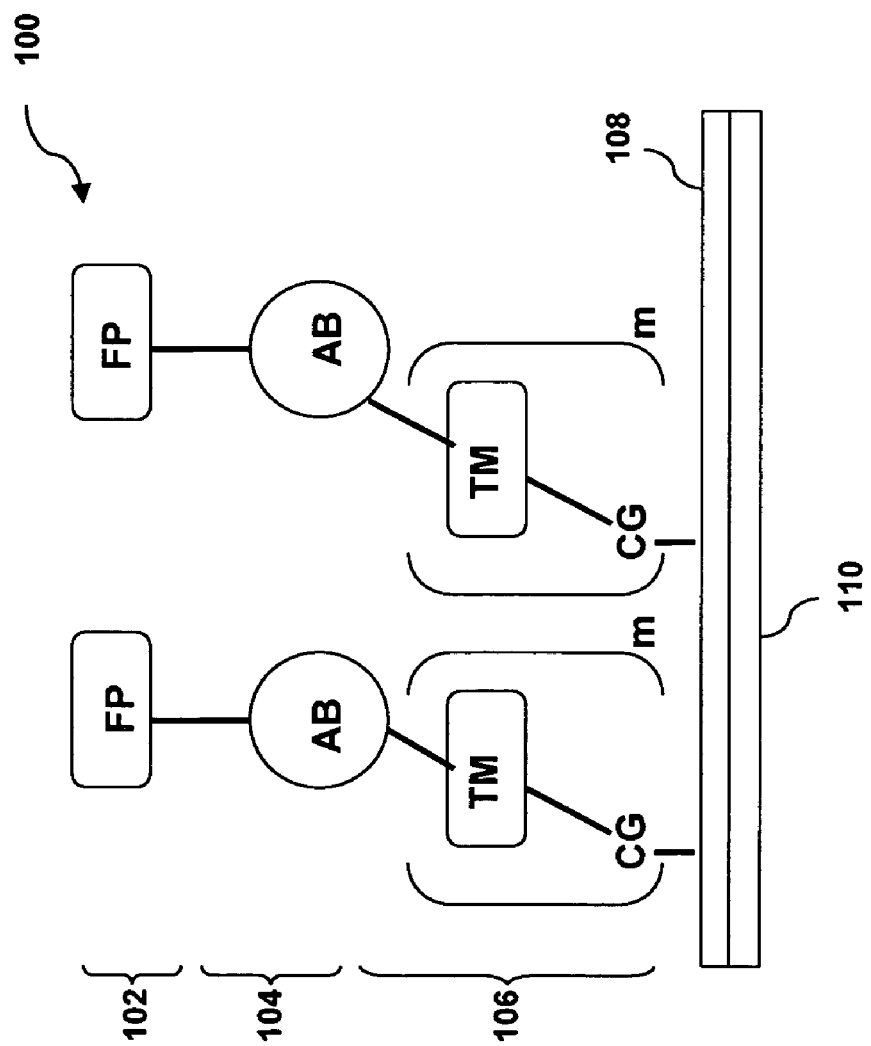
FIG. 1 schematically illustrates various embodiments of an analyte sensor of various embodiments of the present invention.

Prior to further describing the invention, it may be helpful to an understanding thereof to set forth definitions of certain terms to be used herein.

By "biological sample" is meant any sample of biological origin, including samples of biological origin which have been chemically or physically treated, diluted, or concentrated prior to analysis. Examples of biological samples include, but are not limited to, blood serum, blood plasma, whole blood, urine, cerebrospinal fluid, amniotic fluid, saliva, tears, cell lysates and culture media.

As used herein, the term "light" refers to electromagnetic radiation having at least one wavelength in the range between about 200 nanometers (nm) to about 1400 nm. The range includes ultraviolet (UV), visible (vis) and near infrared (NIR) wavelengths. The term light is not limited to coherent electromagnetic radiation (e.g., as provided by a laser) but also includes incoherent radiation (e.g., as provided by a lamp, heater, light emitting diodeetc.). The term light includes both broadband radiation (e.g., light comprising a broad range of wavelengths, some of which may be below about 200 nm or above about 1400 nm,), multiband radiation, and narrowband radiation. As the term "light" includes the infrared portion of the electromagnetic spectrum, it is to be understood that the phrase "irradiation with light" includes heating.

The term "substituted" is intended to describe groups having substituents replacing a hydrogen on one or more atoms, e.g., carbon, nitrogen, oxygen, etc., of a molecule. It will also be noted that the substituents of some of the compounds of this invention include isomeric structures. It is to be understood accordingly that constitutional isomers of particular substituents are included unless indicated otherwise.

Substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic group. Accordingly, the phrase "a substituents as described herein" or the like refers to one or more of the above substituents, and combinations thereof.

The term "alkyl" includes saturated aliphatic groups, which includes both "unsubstituted alkyls" and "substituted alkyls", the latter of which refers to alkyl groups having substituents replacing a hydrogen on one or more carbons of the hydrocarbon backbone. The term "alkyl" includes straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), and cycloalkyl substituted alkyl groups. The term "alkyl" also includes the side chains of natural and unnatural amino acids.

An "alkylaryl" or an "aralkyl" group is an alkyl substituted with an aryl (e.g., phenylmethyl (benzyl)).

The term "aryl" includes 5- and 6-membered single-ring aromatic groups, as well as multicyclic aryl groups, e.g., tricyclic, bicyclic, e.g., naphthalene, anthracene, phenanthrene, etc.). The aromatic ring(s) can be substituted at one or more ring positions with such substituents as described above. Aryl groups can also be fused or bridged with, e.g., alicyclic or heterocyclic rings which are not aromatic so as to form, e.g., a polycycle.

The term "alkenyl" includes unsaturated aliphatic groups analogous in length and possible substitution to the alkyls described above, but which contain at least one double bond. For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl includes both "unsubstituted alkenyls" and "substituted alkenyls", the latter of which refers to alkenyl groups having substituents replacing a hydrogen on one or more carbons of the hydrocarbon backbone.

The term "alkynyl" includes unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl includes both "unsubstituted alkynyls" and "substituted alkynyls", the latter of which refers to alkynyl groups having substituents replacing a hydrogen on one or more carbons of the hydrocarbon backbone.

The term "acyl" includes compounds and groups which contain the acyl radical ($CH_3CO$—) or a carbonyl group. The term "substituted acyl" includes acyl groups having substituents replacing a one or more of the hydrogen atoms.

The term "acylamino" includes groups wherein an acyl group is bonded to an amino group. For example, the term includes alkylcarbonylamino, arylcarbonylamino, carbamoyl and ureido groups.

The term "aroyl" includes compounds and groups with an aryl or heteroaromatic group bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

The term "amide" or "aminocarboxy" includes compounds or groups that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl groups bound to an amino group which is bound to the carbon of a carbonyl or thiocarbonyl group. The terms "alkylaminocarboxy," "alkenylaminocarboxy," "alkynylaminocarboxy," and "arylaminocarboxy" include groups wherein alkyl, alkenyl, alkynyl and aryl groups, respectively, are bound to a nitrogen atom which is in turn bound to the carbon of a carbonyl group.

The term "carbonyl" or "carboxy" includes compounds and groups which contain a carbon connected with a double bond to an oxygen atom, and tautomeric forms thereof. Examples of groups that contain a carbonyl include aldehydes, ketones, carboxylic acids, amides, esters, anhydrides, etc. The term "carboxy group" or "carbonyl group" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl group. For example, the term includes groups such as, for example, aminocarbonyl groups, (wherein a nitrogen atom is bound to the carbon of the carbonyl group, e.g., an amide), aminocarbonyloxy groups, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. groups.

The term "ether" includes compounds or groups that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and groups that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and groups which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or groups wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a group wherein all hydrogens are replaced by halogen atoms.

The term "heteroatom" includes atoms of any element other than carbon or hydrogen. Preferred heteroatoms are nitrogen, oxygen, sulfur and phosphorus.

The term "heterocycle" or "heterocyclic" includes saturated, unsaturated, aromatic ("heteroaryls" or "heteroaromatic") and polycyclic rings which contain one or more heteroatoms. The heterocyclic may be substituted or unsubstituted. Examples of heterocyclics include, for example, benzodioxazole, benzofuran, benzoimidazole, benzothiazole, benzothiophene, benzoxazole, chromene, deazapurine, furan, indole, indolizine, imidazole, isoxazole, isoindole, isoquinoline, isothiazole, methylenedioxyphenyl, napthridine, oxazole, purine, pyran, pyrazine, pyrazole, pyridazine, pyridine, pyrimidine, pyrrole, quinoline, tetrazole, thiazole, thiophene, and triazole. Other heterocycles include morpholino, piprazine, piperidine, thiomorpholino, and thioazolidine.

The term "ORMOSIL" refers to organically modified silicates. One example of an ORMOSIL is polydimethyl siloxane (PDMS). Examples of ORMOSIL gels include gel structures of the formulae (Ia) and (Ib):

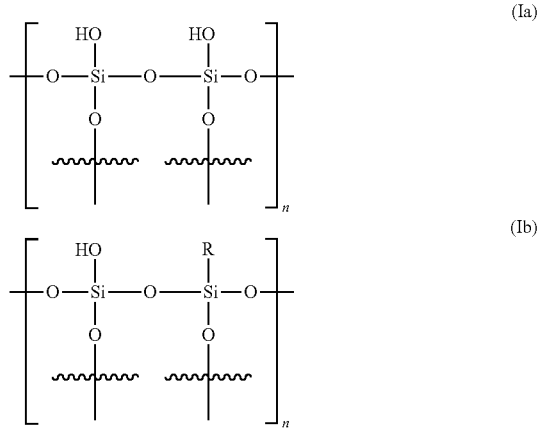

where R represents, e.g., a substituted or unsubstituted: alkyl, alkenyl, aryl, ether, heterocycle, heteroaryl, and combinations thereof. For example, in various embodiments R is a 2,6-pyridinedicarboxylate group.

The terms "polycyclyl" or "polycyclic radical" include groups with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above.

The term "thiocarbonyl" or "thiocarboxy" includes compounds and groups which contain a carbon connected with a double bond to a sulfur atom. The term "thiocarbonyl group" includes groups that are analogous to carbonyl groups. For example, "thiocarbonyl" groups include aminothiocarbonyl, wherein an amino group is bound to the carbon atom of the thiocarbonyl group, furthermore other thiocarbonyl groups include, oxythiocarbonyls (oxygen bound to the carbon atom), aminothiocarbonyl amino groups, etc.

It will be noted that the structures of some of the compounds of this invention include asymmetric carbon atoms. It is to be understood accordingly that the isomers arising from such asymmetry (e.g., all enantiomers and diastereomers) are included within the scope of this invention, unless indicated otherwise. Furthermore, the structures and other compounds, groups and groups discussed in this application also include all tautomers thereof.

Additionally, the phrase "and combination thereof" implies that any number of the listed functional groups and molecules may be combined to create a larger molecular architecture. It is to be understood that when combining functional groups and molecules to create a larger molecular architecture, hydrogens can be removed or added as required to satisfy the valence of each atom.

Detection of Analytes

In the present invention, the detection of analytes combines electrochemical and optical measurement of the analyte-ionophore interaction to provide two different measurements of analyte presence and/or concentration from two different transduction mechanisms provided by the same molecular species, i.e., the analyte sensing molecules having the same fluorophore, analyte binding and linker portions.

The sensors, devices, and methods of the present invention utilize an analyte sensing molecule that can provide both an optical signal (detectable by, e.g., fluorometric techniques) and electrochemical signal (detectable by e.g., potentiometric, amperometric, coulombic, AC analysis, etc. techniques), when an analyte is recognized by an analyte binding portion of the sensing molecule, to determine the presence and/or concentration of an analyte.

Binding of an analyte to the analyte binding portion results in both an electrochemical signal and an optical signal by changing a fluorescence signal from the fluorophore (e.g., by turning on, turning off, increasing, decreasing, shifting, etc, the fluorescence signal). As a result, the binding of an analyte is transduced by two different mechanisms resulting in two signals (fluorescence and electrochemical) that each provide a separate concentration measurement for the analyte. A comparison of these two concentration measurements (e.g., a ratiometric comparison) provides a measure of the reliability of the measurement. In various embodiments, a concentration measurement is not considered reliable unless both the concentration determined from the fluorescence signal and that determined from the electrochemical signal substantially agree. For example, sodium ions are a common interferant with potassium ion electrochemical concentration measurements, and vice versa. In various embodiments, the analyte sensors of the present invention can detect the presence of an interferant ion signal by comparing the fluorescence signal generated by the binding event to the electrochemical signal as the interferant ion is likely to affect the fluorescence signal to a different degree than the electrochemical signal.

In various embodiments, the comparison of the concentration determined from the fluorescence signal and that determined from the electrochemical signal is used to determine when an analyte sensor or microfluidic device of the present invention is in need of calibration or disposal. For example, an analyte sensor or microfluidic device of the present invention can be exposed to a sample of known concentration, and if the two concentrations do not substantially agree the need for calibration is indicated.

In various embodiments, signal transduction in the fluoroionophore is modulated by the photoinduced electron transfer (PET) mechanism. For example, analyte complexation within the binding site of a aza-crown-5 calix[4]arene analyte binding portion suppresses electron transfer to an excited fluorophore and thereby increases the fluorescence intensity, which can be related to the analyte concentration or activity.

A variety of techniques can be used to measure changes in fluorescence arising from the binding of an analyte to the analyte binding portion. In various embodiments, the fluorescence signal intensity is measured. Preferably, one or more bandpass and/or cut-off filters are used to reduce stray light. In various embodiments, the excitation light is modulated and the fluorescence detected by phase sensitive (e.g., phase-locked) detection to facilitate reducing the influence of stray light on the measurements. In various embodiments, changes in fluorescence are measured by measuring the fluorescence lifetimes to facilitate reducing the influence of stray light on the measurements.

Fluorescence intensity measurements are not absolute and should be compared with a standard reference material for calibration. Laser dye with high quantum yields and photochemical stability (e.g., 1,4-Di[2-(5-phenyloxazolyl)benzene] POPOP) are preferred fluorescence intensity standard reference materials.

A variety of electrochemical techniques can be used to measure electrochemical signals arising from the binding of an analyte to the analyte binding portion including, but not limited to, cyclic voltammetry, impedance, capacitance, amperometric, coulombic, AC analysis, and potentiometric measurement techniques. In preferred embodiments of an analyte sensor, microfluidic device or method of the present invention for a medical device, potentiometry is the preferred technique. Potentiometric measurements can also be performed under zero current conditions such that substantially no electrochemistry takes place at the electrode surface.

For example, a potentiometric measurement where the half cell can be represented as:

electrically conductive material|analyte binding portion|sample which can be completed, e.g., with a standard reference electrode. In various embodiments, a microfluidic device of the present invention includes a standard reference electrode (e.g., an Ag/AgCl reference electrode) and a counter electrode (e.g., platinum).

Analyte Sensors and Analyte Sensing Molecules

In various aspects, the present invention provides an analyte sensor comprising an analyte sensing molecule comprising an analyte binding portion, a fluorophore portion, and a linker portion for connecting the analyte molecule to an electrically conductive material on a substrate.

Referring to FIG. 1, in various embodiments, an analyte sensor 100 of the present invention comprises a layer of analyte sensing molecules comprised of a fluorophore portion 102, an analyte binding portion 104 and one or more (m greater than 1) linker portions 106 connecting the analyte sensing molecule 102, 104, 106 to and electrically conductive material 108 covering at least a portion of a substrate 110. A linker portion 106 comprising a tethering molecule TM connecting the analyte sensing molecule to the electrically conductive material 108 with a coupling group CG.

In various embodiments, the analyte sensing molecules form a layer that is substantially monolayer thick film. A variety of techniques exist to assess the properties of a film on a surface, e.g., grazing-angle Fourier transform infrared spectroscopy (grazing-angle FT-IR), quartz crystal gravimetry, atomic force microscopy (AFM), scanning electron microscopy (SEM), cyclic voltammetry, contact angle measurements, and ellipsometry. For example, AFM and ellipsometry can give a relatively direct measure of the thickness of a film. AFM and ellipsometry are preferred methods for determining the thickness of the molecular films of the present invention, and a region of a film is considered to be a monolayer thick if one or more of these AFM and ellipsometry methods indicate that the film is a monolayer thick to a reasonable degree of certainty.

Surface coverage and density can be estimated by combining the results of ellipsometry and quartz crystal gravimetry. In various embodiments, surface coverage can be selected based, for example, on analyte sensor response, fluorescence signal strength, electrochemical signal strength, photochemical stability, and/or electrochemical stability of an analyte sensor. In various embodiments, a microfluidic device of the present invention comprises two or more analyte sensors, or analyte sensor regions, for the same analyte, which have different analyte sensing molecule surface densities. For example, in various embodiments, a microfluidic device of the present invention comprises a microfluidic channel having a first region coated with an analyte sensing molecule at a first density, (e.g., optimized for fluorescence signal intensity) and a second region coated with the analyte sensing molecule at a second density, (e.g., optimized for electrochemical signal intensity).

Figure 2A:
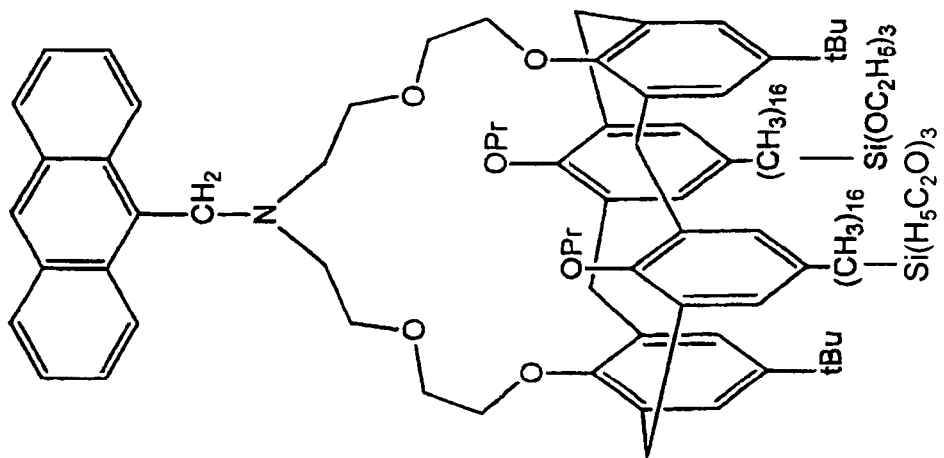
FIG. 2A schematically illustrates various embodiments of an analyte sensing molecule of various embodiments of the present invention.
Figure 2B:
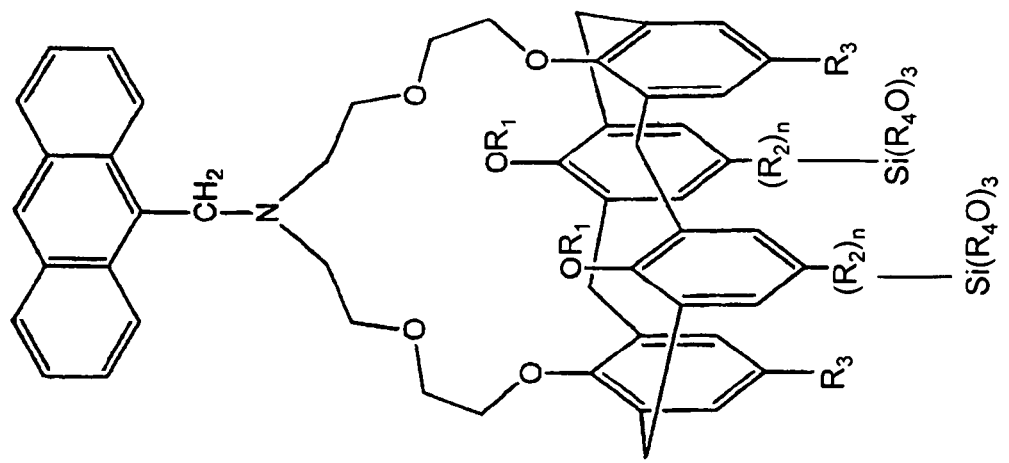
FIG. 2B schematically illustrates an embodiment of an analyte sensing molecule of various embodiments of the present invention, the molecule comprising an anthracene fluorophore portion, and an aza-crown-5 calix[4]arene analyte binding portion with a hexadecyl triethoxysilyl linker portion.

Referring to FIGS. 2A and 2B examples of various embodiments of analyte sensing molecules suitable for use in the present invention are shown. FIG. 2A shows a chemical structure for an analyte sensing molecule comprising an anthracene fluorophore portion, an aza-crown-5 calix[4]ene analyte binding portion, and a linker portion comprising a $C_{16}$ alkyl with a trialkoxysilyl coupling group. Where $R_1$ represents a substituted or unsubstituted alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof; $R_2$ represents a substituted or unsubstituted alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof and preferably a substituted Cn alkyl group where n=1-20; $R_3$ represents a substituted or unsubstituted alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, an aromatic or heteroaromatic group, and combinations thereof; and $R_4$ represents an alkyl.

For example, FIG. 2B shows a chemical structure, for an embodiment of the analyte sensing molecule of 2A, suitable for detecting the presence and/or concentration of potassium ions.

Analyte Binding Portion

Preferably, the analyte binding portion of the sensing molecule is substantially selective for the analyte of interest, e.g., an ionophore where the analyte of interest is an ion. In various embodiments, the analyte binding portion is selective over interferants of concern in a sample by a factor of greater than about 100, and preferably greater than about 1000. In various embodiments, binding portion is selective over interferants of concern in a sample by a factor of greater than about 1000. For example, the typical blood concentration of sodium ions is about 150 mM. For a sensor that is 100 times more sensitive to lithium ions than sodium ions the detection limit of the device for lithium ions is 1.5 mM.

The selectivity of an ionophore for one analyte relative to another, for example, can be evaluated from the selectivity coefficient ($K_{ij}^{Pot}$). Selectivity coefficients can be determined by several methods, such as the Fixed Interference Method (FIM) and Separate Solution Method as described in, for example, E. Bakker et al. *Chem. Rev.* 104, pp. 3083-3132, (1997) the entire contents of which are herby incorporated by reference.

A variety of structures can be used as analyte binding portions in the analyte sensing molecules of the present invention. Preferred analyte binding portions comprise crown ethers, and more preferably aza crown calixarenes, which comprise a convenient attachment site for a fluorophore (or other chromophore) portion via the secondary amine. For example, 14-crown-4 ether, 3-dodecyl-3-methyl-1,5,8,12-tetraoxacyclotetradecane and N-(9-methyl-anthracene)-25, 27-bis(1-propyloxy)-4-p-tert-butylcalix[4]arene-azac-rown-3 are crown ether analyte binding portions, suitable for detecting the presence and/or concentration of lithium ions.

Figure 3B:
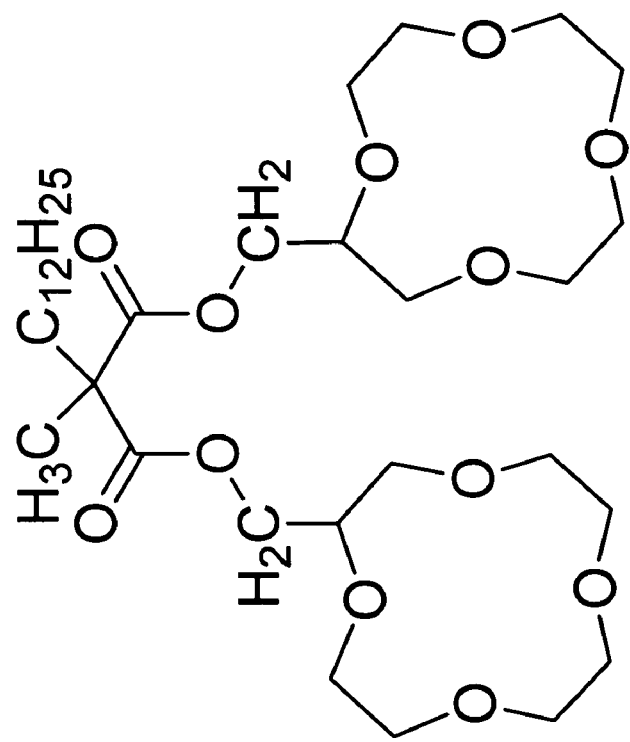
FIGS. 3A-3B depict chemical structures of, respectively, an embodiment of a potassium ion selective ionophore and an embodiment of a sodium ion selective ionophore.
Figure 3A:
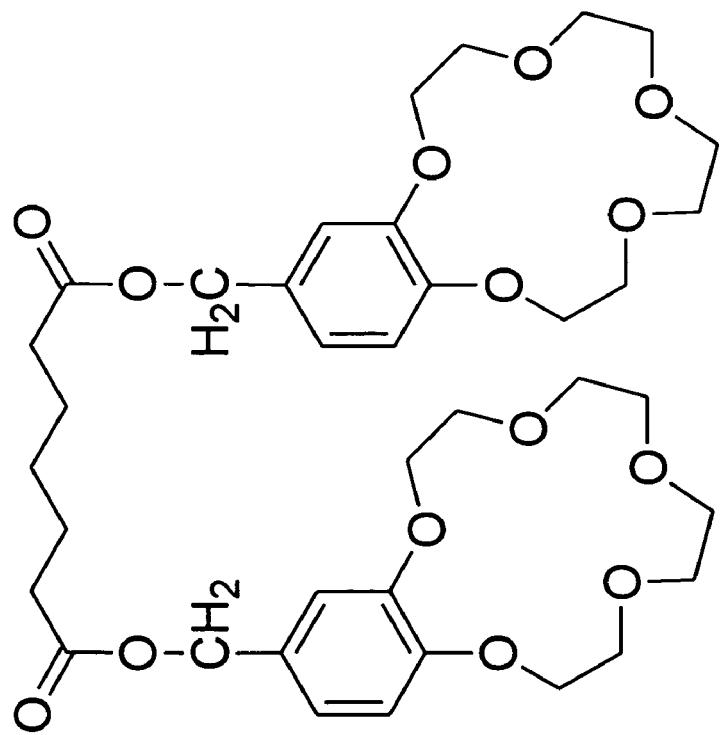
Figure 4:
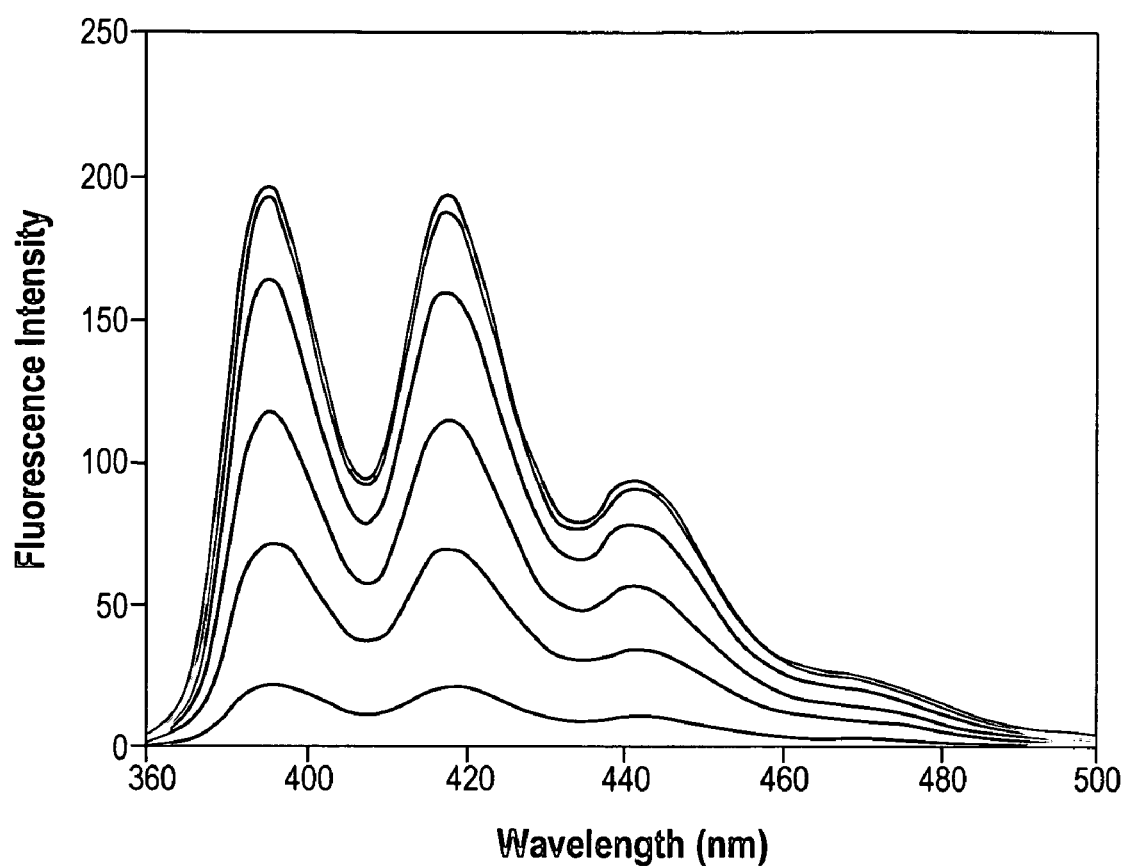
FIG. 4 depicts fluorescence emission spectra of the molecule of FIG. 2B (without the hexadecyl triethoxysilyl groups) excited with 355 nm light in bulk solution at various potassium ion concentrations.

FIGS. 3A-3B show various embodiments of analyte binding portions suitable for various analytes. FIG. 3A shows a chemical structure for an embodiment of a bis(benzo-15-crown-5) ether analyte binding portion, suitable for detecting the presence and/or concentration of sodium ions. FIG. 3B shows a chemical structure for an embodiment of a bis(12-crown-4) ether analyte binding portion, suitable for detecting the presence and/or concentration of potassium ions. Other analyte binding portions include cyclodextrans, segments of specific ribose nuclic acids (RNAs) and deoxyribose nucleic acids (DNAs) and cyclic peptides.

Another consideration in selecting an analyte binding portion is the availability of an electron donor group (e.g., a secondary amine) through which to link the analyte binding portion to the fluorophore portion of the analyte sensing molecule.

Fluorophore Portion

Selection of fluorophore portions can, e.g., be based on fluorescence transition lifetime, shorter lifetime fluorescence transitions typically providing greater intensity and being less sensitive to lifetime reductions via interactions with, e.g., oxygen. For example, for air saturated aqueous solutions, the effect of oxygen on a fluorescence lifetime of about 50 ns is less tabout han 1%. For species with shorter lifetimes the effect is less.

Consideration can also be given to the basic photophysical process by which such molecules fluoresce, i.e., photoinduced electron transfer (PET) where fluorescence is modulated by an intramolecular electron transfer quenching mechanism in which the excited state of the fluorophore is quenched by electron transfer from an electron donating group in the fluoroionophore. A thermodynamic prediction of the feasibility of electron transfer can be made by calculating the free energy of the process using the Rehm-Weller equation:

$$\Delta G_{PET} = E_{oxd/D} - E_{red/A} - \Delta E_{00} - e^2/4\pi \in r \qquad (1),$$

where $E_{oxd/D}$ is the oxidation potential of the electron donor, $E_{red/A}$ is the reduction potential of the electron acceptor, $\Delta E_{00}$ is the energy of the excited state that participates in the electron transfer process, usually a singlet state, and the final term is the Coulombic energy of the ion pair where e is the electron charge, $\in$ is the dielectric constant of the solvent and r is the distance between the two ions.

Examples of suitable fluorophores include, but are not limited to, anthracene, xanthene dyes, 4,4-difluoro-4-boro-3a,4a-diaza-s-indacene, tetramethylrosamine, and anlogs and derivatives thereof. Examples of suitable fluorophores for a monocylic depsipeptide ionophore for ammonium ions include, but are not limited to, aminohodamine B, and N-methyl-4-hydrazino-7-nitrobenzofuran.

Linker Portion: Tether Molecules and Coupling Groups

The linker portion component preferably comprises a molecule capable of forming a self-assembled monolayer on the surface of the substrate to be coated with an analyte sensor film of the present invention. The linker portion can comprise a wide variety of compounds and groups. Preferably, the linker portion is chosen such that its absorption of light, if any, does not detrimentally interfere with the excitation and/or fluorescence of the fluorescence transition of interest of the fluorophore. For example, conjugated molecules can have absorption peaks in regions in which certain fluorescence transitions occur. In addition, in various embodiments, the linker is preferably chosen to facilitate increasing the packing of the analyte binding portion/fluorophore portion "head groups" on the surface.

In various aspects of the present invention, the linker portion comprises an organic tethering molecule and a coupling group, the coupling group for attachment of the linker portion to a surface. Preferred tethering molecules comprise a substituted or unsubstituted $C_1$-$C_{20}$ alkyl group, or a substituted or unsubstituted $C_1$-$C_{20}$ alkyl group wherein one or more of the carbon atoms of the alkyl backbone are replace with one or more of oxygen, nitrogen, sulfur, and phosphorous, a peptide chain (e.g., a helical peptide chain), and combinations thereof.

Examples of preferred coupling groups for attachment of the linker portion to a glass, ORMOSIL gel, and/or metal oxide surface include, but are not limited to, $SiX_3$ or $Si(OR)_3$, where X=Cl, Br, or I, and R=alkyl. For alumina, metal oxide, quartz, glass ($SiO_2$), silicon, and ORMOSIL surfaces, coupling groups can be formed on such surfaces by chemical modification, e.g., to form —$OSiCl_2$—. For example, for polydimethyl siloxane (PDMS) substrates chemical surface modification can be achieved by forming siloxane linkages between the chemical layer deposited and Si—OH bonds on the PDMS surface (which can be created by base or oxidation treatment). Siloxane linkages can be created, e.g., by the reaction of trichlorosilyl- or trialkoxysilyl-functionalized molecules with the surface Si—OH groups. This siloxane chemistry operates with nearly any surface-bound hydroxyl group and is therefore applicable to a wide range of metal oxide substrates, including indium tin oxide (ITO), tin oxide, fluorine-doped tin oxide, tin oxide, and zinc oxide, and the alumina surfaces. Chemical modification of silicon surfaces for attachment of organic molecules is well known and can be used if silicon surfaces are to be coated.

Examples of preferred coupling groups for attachment of the linker portion to various electrically conductive materials include thiolates for gold surfaces (a sulfur atom serving as a surface coupling group); and phosphonates for GaAs and GaN surfaces (a phosphorous atom serving as a surface coupling group); and $SiX_3$ or $Si(OR)_3$ for glass, ORMOSIL gel, and metal oxide surfaces, where X=Cl, Br, or I, and R=alkyl. In general, for non-oxidized metals (e.g., gold, silver, platinum, etc.), organic tethering components can be deposited through the formation of dative bonds between the metal atoms on the surface and thiol or disulfide groups in the molecules to be deposited.

In various embodiments, the procedure for linking an analyte sensing molecule to a surface can be carried out under relatively mild conditions that do not affect the functionality of the molecule. For example, deposition of an analyte sensing molecule comprising a linker portion having a triethoxysilane group onto ITO on a quartz surface can be carried out as follows. The ITO is treated with mild basic conditions to produce reactive hydroxyl functional groups on the surface. Subsequently exposure of the treated ITO surface to the triethoxysilane containing linker, in the presence in the catalytic amount of acid, results in the hydrolysis of the triethoxysilane groups followed by condensation of these groups with the hydroxyl groups on the surface to form a metal-oxygen-silicon bond. In various embodiments of attachment to an ITO material (e.g., on a quartz substrate), the linker portion comprises a sixteen carbon chain terminated in a triethoxysilyl group.

A wide variety of methods can be used to characterize the structure and properties of the analyte sensor layers of the present invention after deposition onto a surface. For example, cyclic voltammetry (CV), impedance measurements, ellipsometry, quartz crystal gravimetry, sessile drop goniometry (contact angle) and grazing incidence IR, can be use to facilitate characterizing the analyte sensor layer. Examples of such measurements are described, e.g., in C. G. F. Cooper et al., Non-Covalent Assembly of a Photoswitchable Surface, *J. Am. Chem. Soc.* 126: 1032-1033 (2004), the entire contents of which are hereby incorporated by reference.

Substrates and Electrically Conductive Materials

A wide variety of substrates and electrically conductive materials can be used in the various aspects of the present invention. In various embodiments, preferred substrate and electrically conductive materials are substantially transparent to the excitation wavelength and the fluorescence wavelength of the fluorophore fluorescence transition of interest. In various embodiments, the substrate and electrically conductive materials are not substantially transparent to the excitation wavelength and the fluorescence wavelength of the fluorophore fluorescence transition of interest, e.g., where the excitation and fluorescence light are not being coupled, into and out of the analyte sensor through the substrate.

A substrate can be, e.g., rigid or flexible. Examples of rigid substrates include, but are not limited to, quartz, glass ($SiO_2$), and silicon wafers. Examples of flexible substrates include, but are not limited to, polyethylene terephthalates (PETs), polyimides, polyethylene naphthalates (PENs), polymeric hydrocarbons, cellulosics, combinations thereof, and the like. PET and PEN substrates may be coated with one or more electrical conducting, oxide layer coatings of, for example, indium tin oxide (ITO), a fluorine-doped tin oxide, tin oxide, zinc oxide, and the like.

Examples of electrically conductive materials include, but are not limited to, metal oxides, such as, e.g., indium tin oxide (ITO), fluorine-doped tin oxide, tin oxide, and zinc oxide, and the like. The electrically conductive material is preferably chosen such that it does not quench the excited state of the fluorescence transition of interest. For example, ITO has several advantages over gold as an electrically conductive material in various embodiments of the present invention. ITO is a substantially transparent material in the visible region of the electromagnetic spectrum (and partially transparent in the ultraviolet) that is typically used in photovoltaic applications as an electrode material. Analyte sensing molecules with, e.g., an anthracene fluorophore, can be deposited on ITO and photoexcited either directly and/or through the ITO material. Another advantage of ITO over gold is that gold is known to quench the excited states of various fluorophores (e.g., anthracene). Chemical deposition techniques for ITO are also known.

Microfluidic Devices

In various aspects, the present invention provides microfluidic devices comprising a substrate having an electrically conductive material covering at least a portion of its surface; an analyte sensor layer covering at least a portion of the electrically conductive material; a reference electrode in electrical contact with the analyte sensor layer; and a counter electrode in electrical contact with the analyte sensor layer. The analyte sensor layer comprising a substantially monolayer thick film of an analyte sensing molecule, the analyte sensing molecule comprising: (a) an analyte binding portion; (b) a fluorophore portion; and (c) a linker portion connecting the analyte sensing molecule to the electrically conductive material.

In various embodiments, one or more channels of a microfluidic device of the present invention are configured for flowing samples, the flow rate being based, for example, on one or more of the removal rate of electrochemical reaction products, maintenance of a constant analyte concentration an the electrode surface, etc.

In various embodiments, a microfluidic device is configured to analyze sample volumes in the range between about 1 nanoliters to about 1 microliter. In various embodiments, a microfluidic device is configured to analyze sample volumes in the range between about 1 microliters to about 25 microliters.

In various embodiments, a microfluidic device of the present invention includes a excitation light source for excitation of the fluorophore portion of the analyte sensing molecule. Examples of suitable light sources include diodes and in particular UV diodes, e.g., 370 nm diodes (Nichia, Japan).

In various embodiments, a microfluidic device of the present invention comprises: (a) a sampling mechanism to obtain a biological sample, which can contain a mechanism to process (e.g., accurately dilute, remove interferants/contaminants, derivatize, etc.) the sample; (b) one or more analyte sensors of the present invention for detecting one or more analytes, the analyte sensor comprising an analyte sensing molecule having an analyte binding portion, a fluorophore portion, and a linker portion, the linker portion connecting the analyte sensing molecule to a substrate; and (c) a calibration component that converts the electrochemical and optical signals generated by an analyte sensing molecule upon binding of the corresponding analyte to a recognized concentration unit for the analyte, there not necessarily being a linear relationship between the transduction mechanism (optical, electrochemical) and the analyte concentration).

Examples of mechanisms to remove interferants/contaminants from a sample include, but are not limited to filtration, precipitation and microdialysis. For example, silica gel can be used to remove large proteins and cellular debris from a sample.

In various embodiments, a microfluidic device comprises one or more regions having photoresponsive wettability that are configured for fluid manipulation. Examples of such regions can be found in pending U.S. patent application Ser. No. 11/014,220, the entire contents of which are hereby incorporated by reference in their entirety. In various embodiments, nano/micro channels having photoresponsive wettability can allow the transport of fluids (e.g., water and other hydrophilic fluids, hydrophobic fluids, or both depending, e.g., on the gradient in surface free energy) by forces, it is believed, without being held to theory, that are similar to those found in capillary action. In various embodiments, the ability to separately control the flow of hydrophilic and hydrophobic liquids in micro or nanochannels can facilitate creating a high degree of complexity in the nano/microfluidic devices produced.

Formation of Micro- and Nanofluidic Structures and Devices

Figure 6:
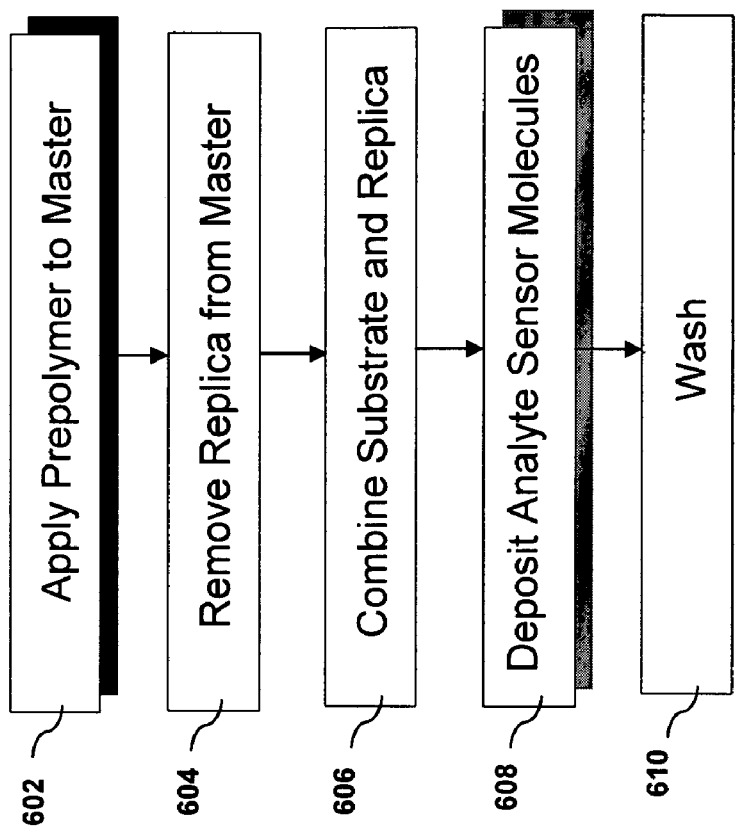
FIG. 6 depicts a schematic flow diagram of a method for forming at least a portion of a microfluidic device of various embodiments of the present invention.
Figure 5:
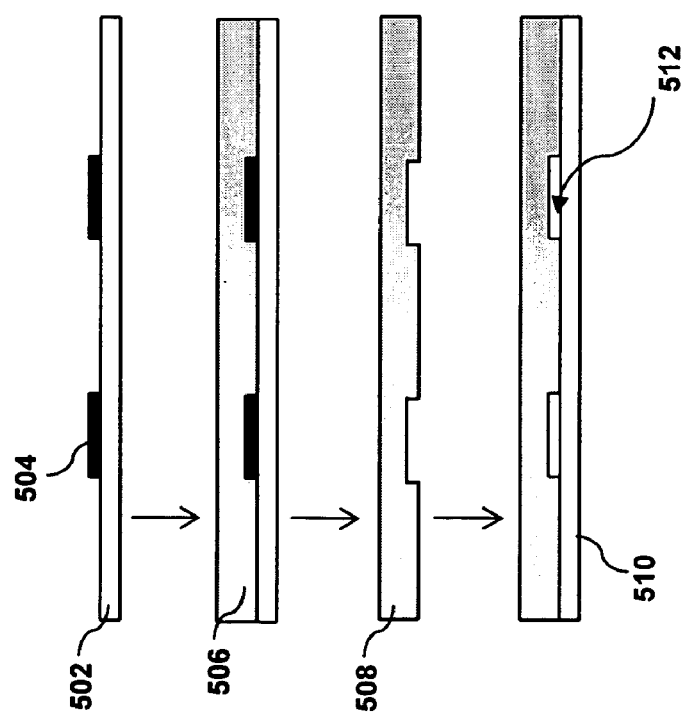
FIG. 5 depicts a scheme for manufacturing a microfluidic channel for a microfluidic device of various embodiments of the present invention.

Referring to FIGS. 5 and 6, various embodiments of methods for fabricating various embodiments of a microfluidic device of the present invention are illustrated using a soft-lithographic fabrication method. In various embodiments, a microfluidic device can be by forming a polymer replica molding of a master template. For example, a master template 502 having structures in relief 504 (e.g., ridges having a width of about 400 nm for forming a channel in a replica molding) is used to create a replica mold. The master template structures can be fabricated, for example, by photolithography. A replica molding can be created by applying a prepolymeric material 506 to the master template 502 (step 602) and curing the polymer.

The cured replica mold 508 is then removed from the master 502 (step 604) and combined with a substrate 510 (step 606), the features in relief on the master forming voids 512 (here in the shape of channels) in the device. The substrate 510 can be patterned or coated with an electrically conductive material after combining the replica and substrate before combination, or both. Preferably, the electrically conductive material is deposited before combination. Similarly, a layer of analyte sensing molecules can be deposited on the electrically conductive material before combination, after combination, or both. In various embodiments, analyte sensing molecules are deposited after combining the replica mold and substrate (step 608), e.g., by flowing a solution of the desired analyte sensing molecules through a desired channel, followed by washing (step 610) to remove, e.g., excess solution.

A preferred polymeric material is polydimethylsiloxane (PDMS). PDMS has several advantageous properties as a polymeric material for a microfluidic device of the present invention. For example, features on the micron scale can typically be reproduced with high fidelity replica molding using PDMS. PDMS is substantially optically transparent down to about 280 nm, facilitating its use in a number of optical signal detection schemes for detecting the fluorescence signals from the analyte sensing molecules (e.g., UV/V is absorbence and fluorescence). It typically cures at a low temperature, about 70° C. It is non-toxic, thereby not prohibiting in vivo implantation of such microfluidic devices. PDMS can be sealed reversible to itself and a range of other materials by making molecular (e.g., van der Waals) contact with a surface or, e.g., irreversibly after exposure, e.g., to air plasma by formation of covalent bonds. Since PDMS is elastomeric, it can also comform to smooth non-planar surfaces increasing the range of structures which can be molded.

In various embodiments of forming a microfluidic device of the present invention, a PDMS polymeric replica mold is prepared by applying a prepolymer onto a master template and curing for about 3 hours at about 70° C. The PDMS replica is then removed from the template and sealed to a quartz substrate patterned with ITO by first treating the ITO surface with a dilute alkaline solution and applying the replica mold to the treated surface.

Figure 7:
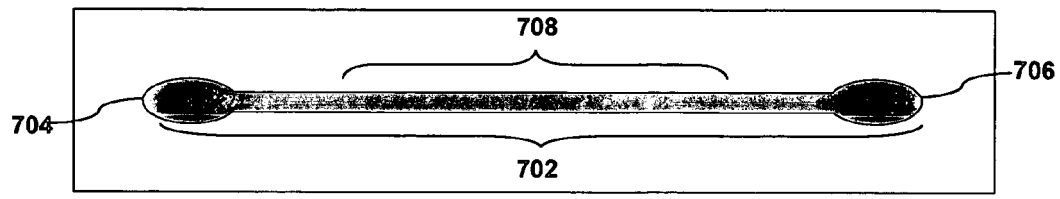
FIG. 7 schematically depicts an embodiment of a microfluidic channel for a microfluidic device of various embodiments of the present invention.
Figure 8:
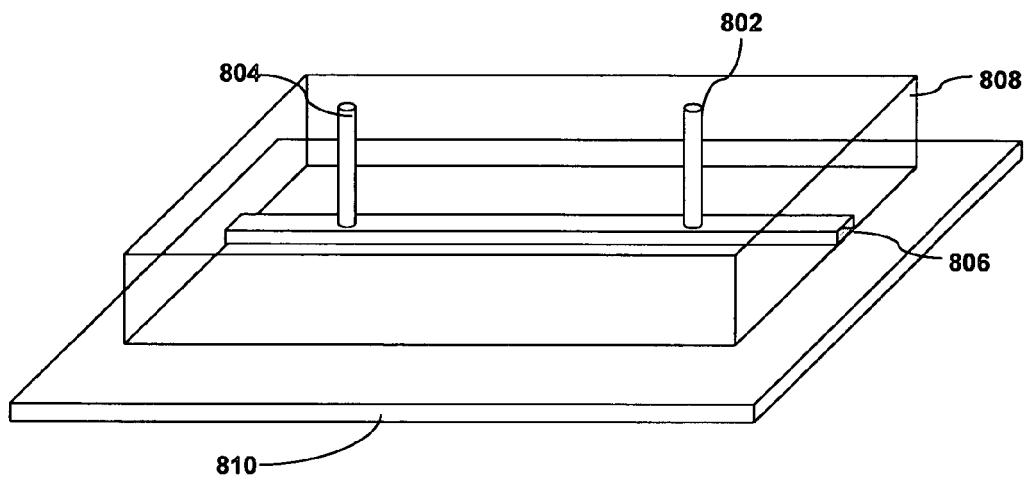
FIG. 8 schematically depicts an embodiment of microfluidic device of various embodiments of the present invention.

An example of a simple structural element of a microfluidic device is illustrated in FIG. 7 in a plane view. This simple structural element comprises a channel 702 having a sample inlet port 704 and a sample outlet port 706. A portion of the channel bed 708 is coated with an electrically conductive material to which is attached an analyte sensor layer. This portion 708 forming a measurement region for this structure. Such a configuration can be utilized with a flowing sample, a stationary sample, or combinations thereof. Counter and reference electrodes can be placed with this simple structure in a wide variety of ways. For example, counter and reference electrodes for this microfluidic device structure can be placed in a collecting reservoir (e.g., at sample out), formed through the overlying replica mold structure, etc., or combinations thereof. For example, referring to FIG. 8, in various embodiments, a counter electrode 802 (e.g., a platinum wire) and a reference electrode 804 (e.g., an Ag/AgCl electrode) in contact with a channel 806 are formed through the overlying layer 808 formed by the replica mold on the substrate 810. The use of a substrate and electrically conductive material substantially transparent to one or more of the excitation and fluorescence wavelengths of the fluorophore, e.g., facilitates optical excitation and fluorescence detection through the back side, side opposite the overlying layer 808, of the substrate 810.

Figure 9:
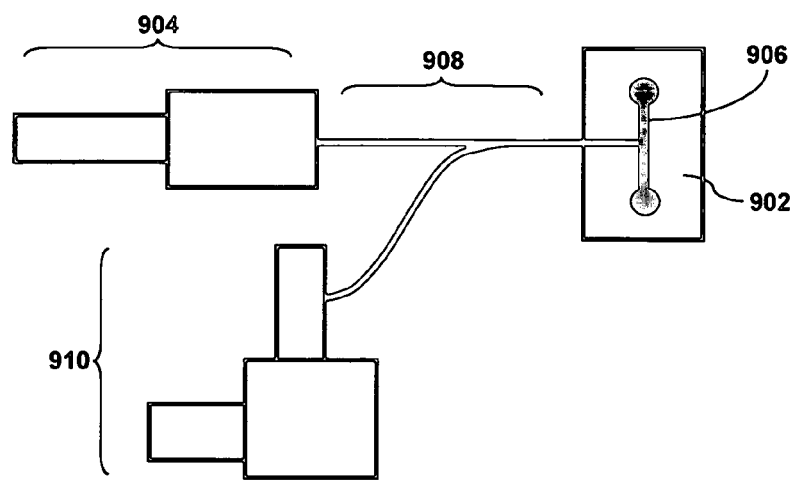
FIG. 9 schematically depicts an embodiment of microfluidic device of various embodiments of the present invention having a system for acquisition of fluorescence from the microfluidic device.

Referring to FIG. 9, an optical excitation and fluorescence detection structure are schematically illustrated. It is to be understood that although these structures are illustrated as not on the substrate 902, the functionality of many if not all of these structures can be integrated on the microfluidic device. In various embodiments, an optical excitation light source 904 (e.g., a Xenon Arc lamp with monochrometer, laser, etc.) is directed to the analyte sensor 906 using a bifrucated fiber optic 908 and fluorescence collected at the common end of the fiber optic and coupled to a detector 910 (e.g., an emission monochrometer with an intensified diode array, photomultiplier, etc.) for detection of the optical signals generated by the analyte sensing molecules.

EXAMPLES

Aspects of the present inventions may be further understood in light of the following examples, which are not exhaustive and which should not be construed as limiting the scope of the present inventions in any way.

Example 1

Potassium Ion Analyte Sensor

Potassium ions ($K^+$) are an important analyte in the healthcare field. This analyte is a predominant intercellular cation with an average concentration of 150 mM, whereas the normal mean serum concentration range is between 3.5 to 5.1 mM. Maintenance of this concentration gradient is critical in the adequate functioning, for example, cardiac, muscle and nerve transmission process and is governed by the sodium, potassium ATPase pump. Potassium levels are routinely determined using serum (or plasma) and urine samples. Deviations from normal levels have and are used as supportive indicators for a multitude of disease states. For example, changes in potassium serum levels can be indicative of the following conditions: hypokalemia due to such factors as insulin therapy and renal losses; hypokalemia due to acute and chronic renal failure; and Addison's disease. Increase in potassium levels in urinary samples can be indicative of primary renal diseases, renal tubular syndromes, as well as metabolic acidosis and alkalosis. Variations of the potassium level due to these conditions can have significant impact upon the myocardium as well as the neuromuscular system resulting in sever weakness, paralysis, and life threatening arrhythmias.

A. Analyte Sensing Molecule

The analyte sensing molecule in this example comprises aza-crown-5 calix[4]ene, a potassium sensitive ionophore as the analyte binding molecule, and anthracene as the fluorophore. The linker portion comprises a hexadecyl triethoxysilyl. This analyte sensing molecule is illustrated in FIG. 2B. The analyte sensing molecule in this example exhibits an increase in fluorescence by the in response to potassium binding by the ionophore, operating as an on-off fluorescence switch mechanism. Work on this ionophore/fluorophore combination in solution and PVC membranes indicates that it shows a ten-fold increase in fluorescence upon binding of potassium and a selectivity over sodium ions of better than 1000.

B. Synthesis of the Analyte Sensing Molecule and Attachment to Surface

The combined analyte binding portion and fluorophore can be synthesized as described, e.g., in the Ph.D. dissertation of John S. Benco, *The Rational Design and Synthesis of Ionophores and Fluoroionophores for the Selective Detection of Monovalent Cations*, Worcester Polytechnic Institute, (1993). The linker portion can be attached to the ionophore portion by substitution reactions with α-bromo-ω-vinyl molecule ($C_{16}$) to produce long alkyl chains connected to the calixarene through an ether linkage and leaving the reactive vinyl group for further substitution (e.g., substitution of a coupling group). This vinyl group can be converted, e.g., to a triethoxysilyl group by hydrosylation or to a trichlorosilyl group. Each of these coupling groups can undergo hydrolysis condensation reactions with surface based hydroxyl groups such as, e.g., those available on ITO, to covalently attach the analyte sensing molecule to the surface. The analyte sensing molecule of this example is illustrated in FIG. 2B, where the linker groups have yet to be attached to the ITO surface.

C. Characterization of Analyte Sensor Layer on ITO

Cyclic voltammetry measurements can be used to characterize the analyte sensor layer on the ITO. Such electrochemistry experiments can be carried out with an EG&G Princeton Applied Research Potentiostat/Galvanostat Model 273. A three-electrode setup can be used with the ITO layer-ionophore as the working electrode, a SCE as the reference electrode, and platinum wire as the counter electrode. The analyte sensor layer can be contacted with an alligator clap, and an area of 1 cm² is a typical sample area to measure. The CV measurements are typically carries out in aqueous solutions using 1 mM potassium ferrocyanide or ferrocene as a redox active species and 50 mM potassium chloride as a supporting electrolyte. To limit noise, the electrochemical cell can be placed inside a Faraday cage. The cyclic voltammetry curves are typically obtained in the range of −0.5 to 0.7 V, at various scan rates.

Impedance measurements can be carried out using substantially the same three-electrode setup of the CV measurement. The electrolyte typically used is a 0.1 M solution of $Na_2SO_4$ in deionized water. A 1255-HF frequency response analyzer can be used in combination with a EG&G Princeton Applied Research Potentiostat/Galvanostat Model 273 to carry out the measurements. The experiment can be typically carried out at a fixed potential of −0.5 V, with an amplitude of 20 mV, over a frequency range of 100,000 to 0.01 Hz, with 20 points collected per decade. The working electrode area is 1 cm². The impedance data can be plotted as Nyquist and Bode plots, and analyzed using a complex least-squares analysis.

Analyte sensor layer thickness measurements can be carried out with a Manual Photoelectric Rudolf 439L633P ellipsometer (Rudolph Instruments, Fairfield, N.J., USA). Measurements are typically obtained at a 70° angle of incidence using a HeNe laser (principle wavelength 632.8 nm).

Contact angle measurement values can yield a qualitative determination of surface hydrophobicity. Such measurements can be carried out with a Rame-Hart Model 100-00 Goniometer using, e.g., less than 1 microliter droplets of water.

Surface coverage can be estimated by combining the results of ellipsometry and quartz crystal gravimetry, the latter can be carried out with a Maxtech RQCM quartz crystal microbalance.

D. Detection of Potassium Ion in a Microfluidic Device

Figure 10:
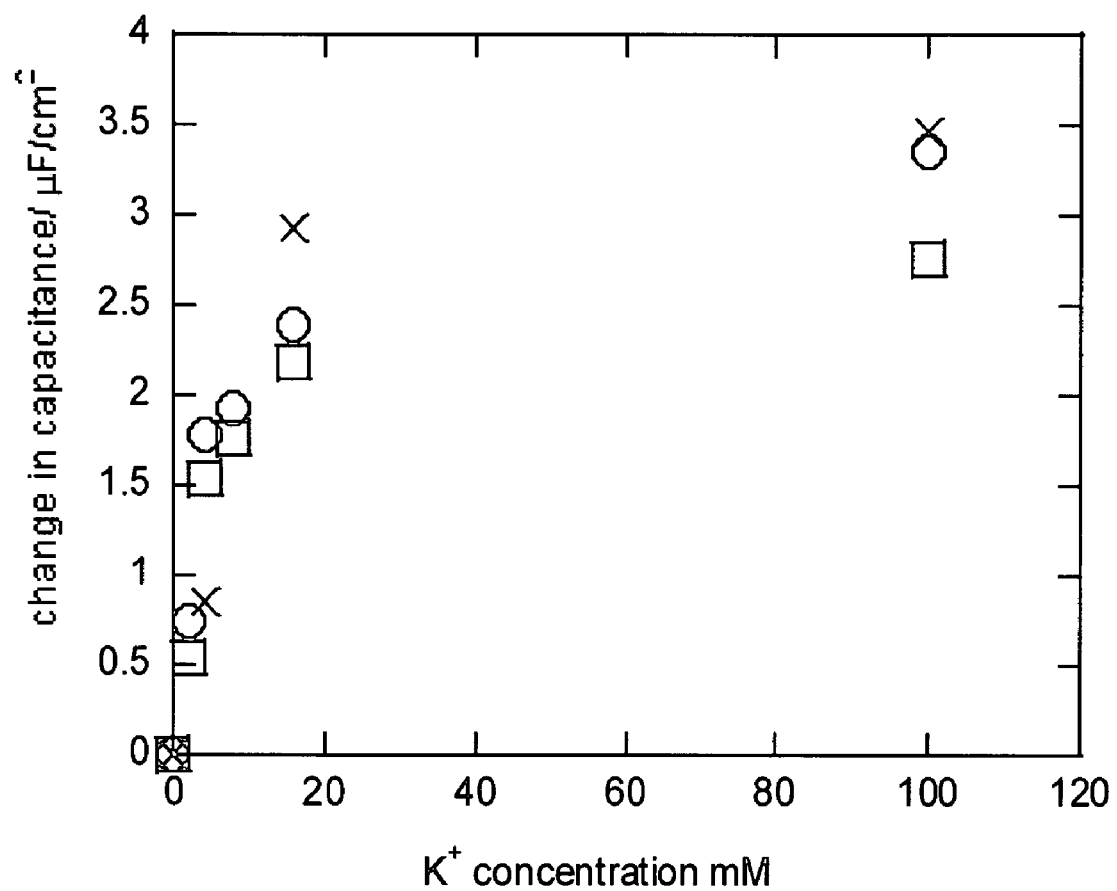
FIG. 10 depicts a plot of the change in capacitance values of the SAM of three different samples of a device of Example 1 as a function of potassium ion concentration.

To demonstrate the detection of alkali metal ions in a microfluidic device a SAM was synthesized using a non specific ion sensor 11-mercapto-1-(aza-18-crown-6)-undecane-1-one. The microfluidic devices consisted of a microfluidic channel with a reservoir at one end. The reference (Ag wire) and counter electrodes (Pt wire) were placed in contact with the solution in the reservoir. Results from this device are depicted in FIG. 10 for three different samples of this device each prepared in substantially the same manner. The results for all three samples show that the capacitance of the SAM is responsive to a change in the potassium ion concentration.

E. Storage

The response of the analyte sensor of this example is not expected to change if stored in a cool dark environment.

Example 2

Lithium Ion Analyte Sensor

Monitoring of $Li^+$ in blood is necessary for patients who suffer from manic depressive and hyperthyroidism illnesses and who are treated with lithium salts. This example illustrates the detection of lithium ion concentration in solution.

Monolayers of hexadecanethiol coupled to a bicyclic molecule with the ability to selectively complex $Li^+$ ions were fabricated. The ability of these monolayers to function as sensors was shown by cyclic voltammetry and impedance spectroscopy techniques. Impedance experiments in the absence of a redox probe (i.e. only supporting electrolyte) provided reproducible data that shows a change in monolayer capacitance upon ion complexation. The compound showed selectivity for complexation of $Li^+$ ions over other ions, with log $K_{Li+,Na+}$~−1.30 and log $K_{Li+,K+}$~−0.92.

All reagents and solvents for synthesis were purchased from Aldrich and used as received unless otherwise noted. N-Fmoc-iminodiacetic acid was purchased from Fluka Chemical Corporation (Milwaukee, Wis.). Poly(vinyl chloride) high molecular weight (PVC) and dioctyl phthalate (DOP) were purchased from Fluka (Bush, Switzerland). Electrolyte solutions were freshly prepared using high-purity Millipore deionized water (18 MΩ.cm). NMR spectra were obtained in an Avance Bruker spectrometer at 400 MHz for proton and 100 MHz for $^{13}C$. All NMR spectra were obtained in $CDCl_3$ solutions unless otherwise indicated.

A. Analyte Sensing Molecule

Figure 11A:
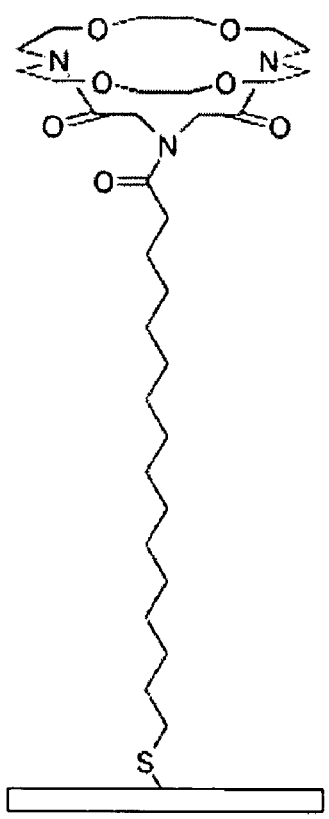
FIGS. 11A and 11B schematically depict the structure of the $Li^+$ sensors used in Example 2.

The analyte sensing molecule in this example comprises 4,7,13,16-tetraoxa-1,10,21-triaza-bicyclo[8.8.5]tricosane-19,23-dione, a lithium sensitive ionophore as the analyte binding molecule. The linker portion comprises a hexadecanethiol chain. FIG. 11A schematically illustrates the attachment of the analyte sensing molecule of this example to a gold surface through a sulfur atom. The hexadecanethiol molecule was used to form a relatively ordered self-assembled monolayer on gold, with the bicyclic moieties exposed on the surface. The lithium ion binding ability of the surface-bound sensor was monitored by cyclic voltammetry and impedance spectroscopy.

Figure 11B:
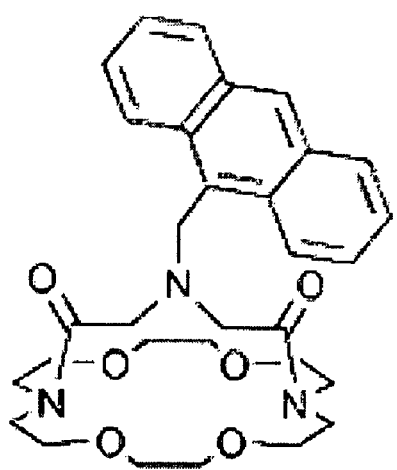

The 4,7,13,16-tetraoxa-1,10,21-triaza-bicyclo[8.8.5]tricosane-19,23-dione ionophore was also been modified to contain a anthracene fluorophore that transduces the binding of ions via enhanced fluorescence emission. The modified ionophore is schematically shown in FIG. 11B. The analyte sensing molecule in this example exhibits an increase in fluorescence by the in response to lithium binding by the ionophore, operating as an on-off fluorescence switch mechanism.

B. Synthesis of the Analyte Sensing Molecule

The synthesis of various compounds used in this example is substantially outlined in Scheme 1 and as follows.

9H-9-fluorenylmethyl-19,23-dioxo-4,7,13,16-tetraoxa-1,10,21-triaza bicyclo [8.8.5]tricosane-21-carboxylate In a round bottom flask, 1.78 g (5 mmol) of N-Fmoc-iminodiacetic acid was dissolved in 15 mL (206 mmol) of thionyl chloride and the solution was heated at reflux for 30 min. The excess of thionyl chloride was then removed under reduced pressure at 40° C., and the residue was dissolved in 250 mL of dichloromethane. A sample of 1.31 g (4.9 mmol) of diaza-18-crown-6 and 2.6 mL (14.4 mmol) of diisopropylethylenediamine (DIPEA) was added to the dichloromethane solution. The mixture was stirred for 7 hours at room temperature. DIPEA and the solvent were removed by evaporation of the mixture under reduced pressure, and the residue was redissolved in 100 mL of dichloromethane. The solution was washed three times with 100 mL of 2 N HCl, once with 100 mL of water and finally dried over anhydrous $MgSO_4$. The solvent was finally removed under reduced pressure to yield a white solid residue, which was purified by flash column chromatography (Biotage Flash 40 column 15 cm×7 cm, $CH_2Cl_2$:$CH_3OH$ 15:1). Yield: 2.0 g (70%). $R_f$=0.5 ($CH_2Cl_2$:$CH_3OH$ 15:1). $^1$H-NMR (400 MHz, $CDCl_3$), δ 2.71-2.73 (m, 2H), 2.98-3.00 (m, 2H), 3.54-3.83 (m, 16H), 3.90-3.94 (m, 2H), 4.03-4.07 (d, J=16.7 Hz, 1H), 4.11-4.15 (d, J=16.7 Hz, 1H), 4.25-4.32 (m, 2H), 4.40-4.45 (m, 2H), 4.51 (dd, J=6.1, 3.8 Hz, 1H), 4.58 (d, J=16.7 Hz, 1H), 4.80 (d, J=16.7 Hz, 1H), 7.22-7.40 (m, 4H), 7.60-7.64 (m, 2H), 7.73 (d, J=7.6 Hz, 2H); $^{13}$C-NMR (100 MHz, $CDCl_3$), δ 42.3 (CH), 42.7 ($CH_2$), 42.8 ($CH_2$), 44.2 ($CH_2$), 44.4 ($CH_2$), 45.4 ($CH_2$), 45.5 ($CH_2$), 62.5 ($CH_2$), 62.7 ($CH_2$), 63.2 ($CH_2$), 65.5 ($CH_2$), 65.6 ($CH_2$), 66.1 ($CH_2$), 66.1 ($CH_2$), 66.7 ($CH_2$), 66.9 ($CH_2$), 114.9 (CH), 115.0 (CH), 120.4 (CH), 120.7 (CH), 122.2 (CH), 122.3 (CH), 122.6 (CH), 122.8 (CH), 123.0 (CH), 136.4 (CH), 136.4 (CH), 139.2 (CH), 139.6 (CH), 152.4 (C=O), 163.9 (C=O), 164.2 (C=O).

Scheme 1

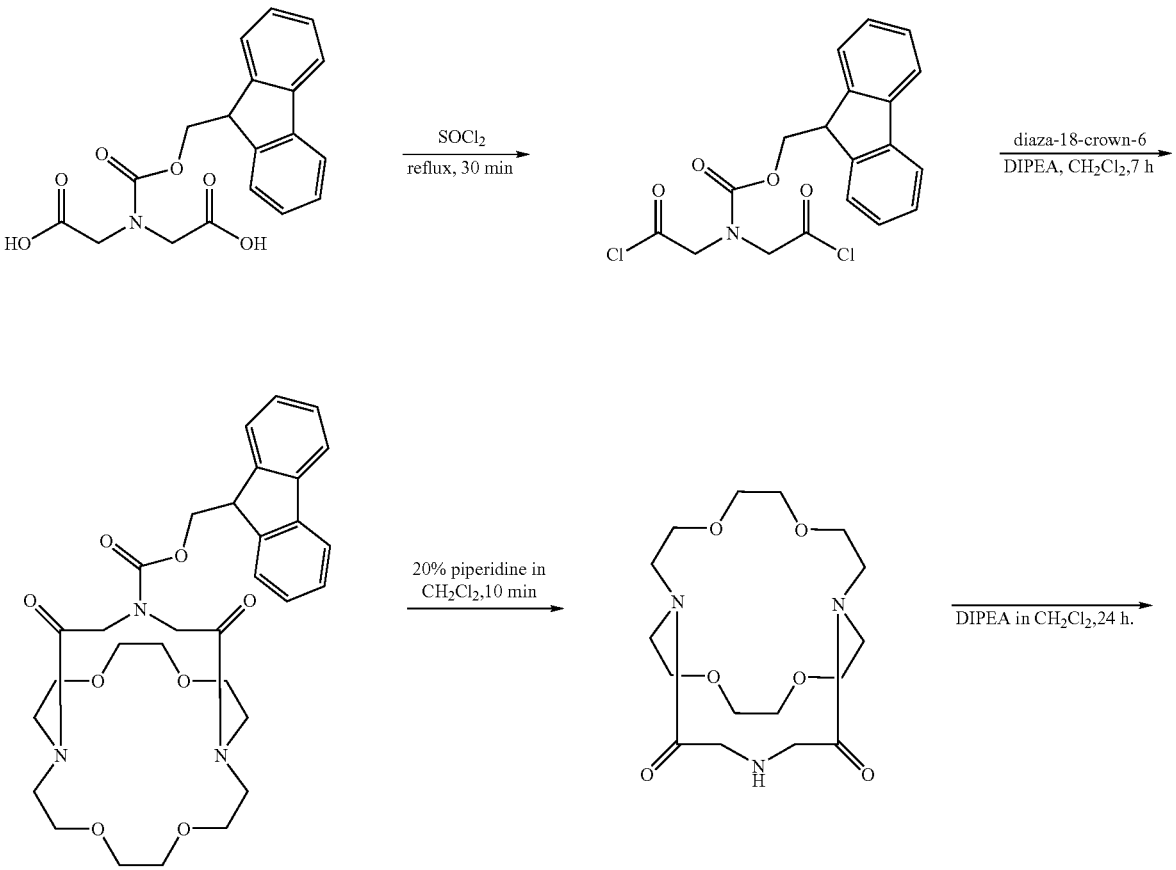

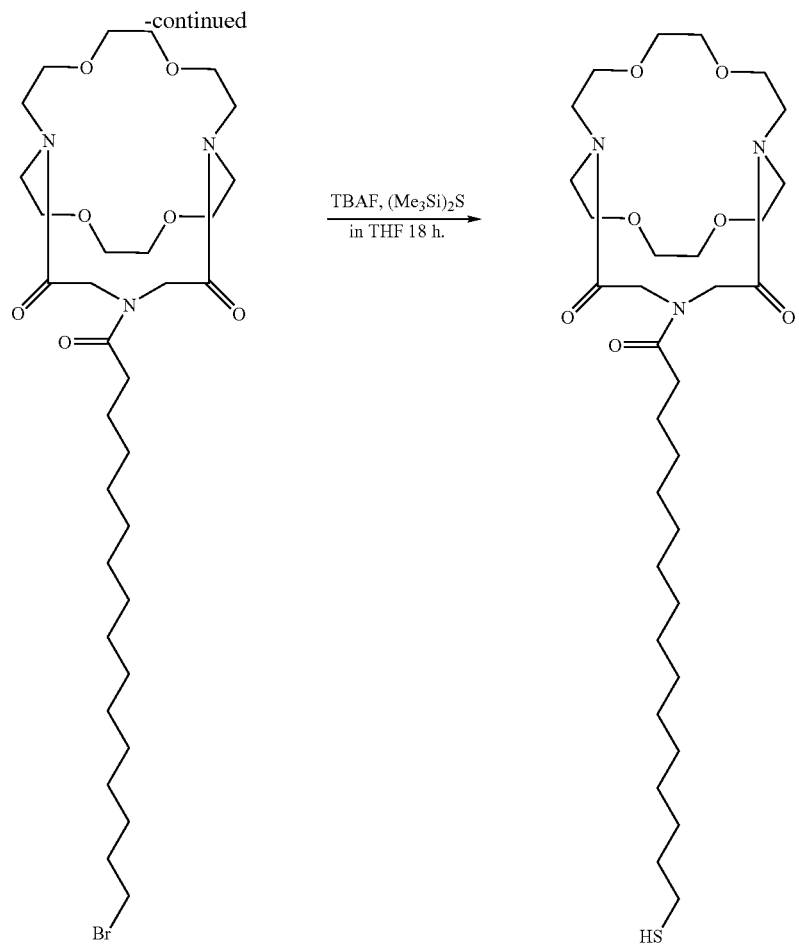

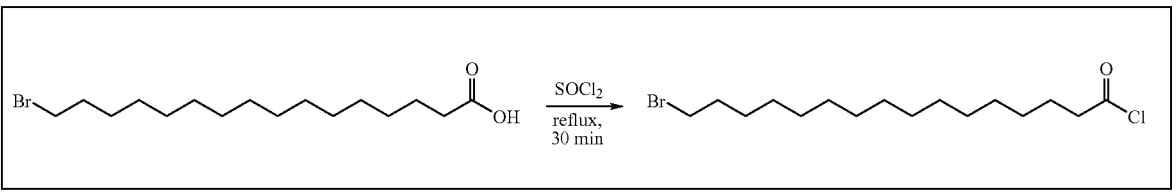

4,7,13,16-tetraoxa-1,10,21-triaza-bicyclo[8.8.5]tricosane-19,23-dione

In a round bottom flask, 0.49 g (0.84 mmol) of 9H-9-fluorenylmethyl-19,23-dioxo-4,7,13,16 tetraoxa-1,10,21-triazabicyclo[8.8.5]tricosane-21-carboxylate was dissolved in 20 mL of 20% piperidine in $CH_2Cl_2$, and the solution was stirred for 30 min. The solvent was removed under reduced pressure at 40° C., to yield a light yellow gum. The product was purified by flash chromatography (Biotage Flash 40 column 15 cm×7 cm, $CH_3OH$: $Et_3N$ 25:1) to yield 0.28 g of a white solid. Yield (93%). $R_f$=0.4 (25:1 MeOH: $Et_3N$); $^1$H-NMR (400 MHz, $CDCl_3$): δ 2.68-2.74 (m, 2H), 2.90-2.96 (m, 2H), 3.48-3.70 (m, 18H), 3.77-3.85 (m, 2H), 3.89-3.94 (m, 2H), 4.33-4.37 (m, 2H); $^{13}$C-NMR (100 MHz, $CDCl_3$): δ 48.5 (2 $CH_2$), 50.0 (2 $CH_2$), 50.5 (2 $CH_2$), 68.1 (2 $CH_2$), 70.7 (2 $CH_2$), 71.0 (2 $CH_2$), 72.7 (2 $CH_2$), 171.8 (2 C=O).

21-(16-bromo-hexadecanoyl)-4,7,13,16-tetraoxa-1,10,21 triazabicyclo[8.8.5]tricosane-19,23-dione In a round bottom flask, 0.99 g (3 mmol) of 16-bromohexadecanoic acid was dissolved in 15 mL (15 mmol) of thionyl chloride. The solution was heated at reflux for 30 minutes. Thionyl chloride was removed under reduced pressure, at 40° C. The residue was dissolved in 30 mL of dichloromethane. To this solution, 1.11 g (3.1 mmol) of 4,7,13,16-tetraoxa-1,10,21-triaza-bicyclo[8.8.5]tricosane-19,23-dione and 1.4 mL (7.7 mmol) of DIPEA were added. The mixture was stirred at room temperature for 1 day. DIPEA and solvent were removed from the solution by evaporation of the solvent mixture under reduced pressure, and the residue was redissolved in 100 mL of dichloromethane. The solution was washed three times with 100 mL of 2 N HCl, once with 100 mL of water, and finally dried over anhydrous $MgSO_4$. The solvent was removed under reduced pressure and the product was finally purified by column chromatography ($CH_2Cl_2$: $CH_3OH$ 20:1) to afford a yellow oil. Yield: 0.96 g (72%). $R_f$:0.32 ($CH_2Cl_2$:$CH_3OH$ 20:1), $^1$H-NMR (400 MHz, $CDCl_3$): δ 1.24-1.42 (m, 22H), 1.65-1.67 (m, 2H), 1.82-1.89 (m, 2H), 2.38-2.42 (dd, J=15.41, 7.58 Hz, 2H), 2.66-2.83 (m, 2H), 2.97-3.05 (m, 2H), 3.41 (t, J=6.82, 2H), 3.47-3.72 (m, 16H), 3.82-3.99 (m, 4H), 4.22-4.40 (m, 4H). $^{13}$C-NMR (100 MHz, $CDCl_3$): δ 25.5 ($CH_2$), 28.5 ($CH_2$), 29.1 ($CH_2$), 29.8

(CH$_2$), 29.8 (CH$_2$), 29.9 (CH$_2$), 30.0 (CH$_2$), 33.1 (CH$_2$), 33.2 (CH$_2$), 34.5 (CH$_2$), 45.8 (CH$_2$), 48.7 (CH$_2$), 49.6 (CH$_2$), 50.3 (CH$_2$), 50.8 (CH$_2$), 50.8 (CH$_2$), 67.3 (CH$_2$), 67.8 (CH$_2$), 70.3 (CH$_2$), 70.9 (CH$_2$), 71.1 (CH$_2$), 71.3 (CH$_2$), 71.8 (CH$_2$), 72.6 (CH$_2$), 168.9 (C=O), 169.5 (C=O), 174.5 (C=O).

21-(16-mercapto-hexadecan-1-oyl)-4,7,13,16-tetraoxa-1,10,21 triazabicyclo [8.8.5]tricosane-19,23-dione Direct mercapto-dehalogenation of the alkyl halide was done according to the procedure reported by Fox et. al.[20] In a round bottom flask, 0.80 g (1.2 mmol) of 21-(16-bromo-hexadecanoyl)-4,7,13,16-tetraoxa-1,10,21 triaza bicyclo [8.8.5] tricosane-19,23-dione was dissolved in 1 mL of dry THF and cooled to −10° C. for 10 min. Then, 0.29 mL of hexamethyldisilathiane ((Me$_3$Si)$_2$S, 1.4 mmol) and 1.29 mL of tetrabutylammonium fluoride (TBAF, 1.3 mmol, 1.0 M solution in THF with 5% water) were added. The reaction mixture was allowed to warm to room temperature while being stirred for 3 hours. The reaction mixture was diluted with 50 mL of dichloromethane and washed three times with saturated aqueous ammonium chloride. The product was obtained by column chromatography (CH$_2$Cl$_2$:methanol 20:1) as a yellow oil. Yield: 0.47 g (63%). R$_f$=0.27 (20:1 CH$_2$Cl$_2$:CH$_3$OH); $^1$H-NMR (400 MHz, CDCl$_3$), δ 1.24-1.43 (m, 22H), 1.60-1.66 (m, 4H), 2.37-2.41 (dd, J=15.41, 7.58 Hz, 2H), 2.51 (q, J=7.58 Hz, 2H), 2.67-2.87 (m, 2H), 2.99-3.06 (m, 2H), 3.50-3.73 (m, 16H), 3.78-3.96 (m, 4H), 4.22-4.38 (m, 4H). $^{13}$C-NMR (100 MHz, CDCl$_3$), δ 24.9 (CH$_2$-SH), 25.4 (CH$_2$), 28.4 (CH$_2$), 28.7 (CH$_2$), 29.1 (CH$_2$), 29.4 (CH$_2$), 29.7 (CH$_2$), 29.8 (CH$_2$), 29.8 (CH$_2$), 29.9 (CH$_2$), 29.9 (CH$_2$), 33.0 (CH$_2$), 33.1 (CH$_2$), 34.4 (CH$_2$), 34.5 (CH$_2$), 45.8 (CH$_2$), 48.6 (CH$_2$), 49.4 (CH$_2$), 50.0 (CH$_2$), 50.6 (CH$_2$), 50.7 (CH$_2$), 67.2 (CH$_2$), 67.7 (CH$_2$), 70.3 (CH$_2$), 70.8 (CH$_2$), 71.1 (CH$_2$), 71.2 (CH$_2$), 71.7 (CH$_2$), 72.5 (CH$_2$), 168.7 (C=O), 169.4 (C=O), 174.4 (C=O). ESI-MS: m/z C$_{32}$H$_{59}$N$_3$O$_7$Na (M+Na)$^+$ calculated at 652.9, experimental: 652.5.

C. Preparation of Surface and SAM

Gold slides were purchased from Evaporated Metal Films (EMF, Ithaca, N.Y.). The slides have dimensions of 25 mm×75 mm×1 mm with cut edges. They are fabricated on a float glass substrate, coated with 50 Å of chromium followed by 100 Å of gold. The substrates were cut in different sizes according to experimental needs. The slides were cleaned in piranha solution (70% concentrated sulfuric acid and 30% hydrogen peroxide) for 15 minutes, rinsed with water and ethanol, and dried with nitrogen prior to use. SAMs of the target molecule were prepared by immersing a clean gold slide in a 1-3 mM solution of the thiol in ethanol for up to 48 hours. The SAMs were rinsed with ethanol and dried with a stream of nitrogen before use.

Figure 12:
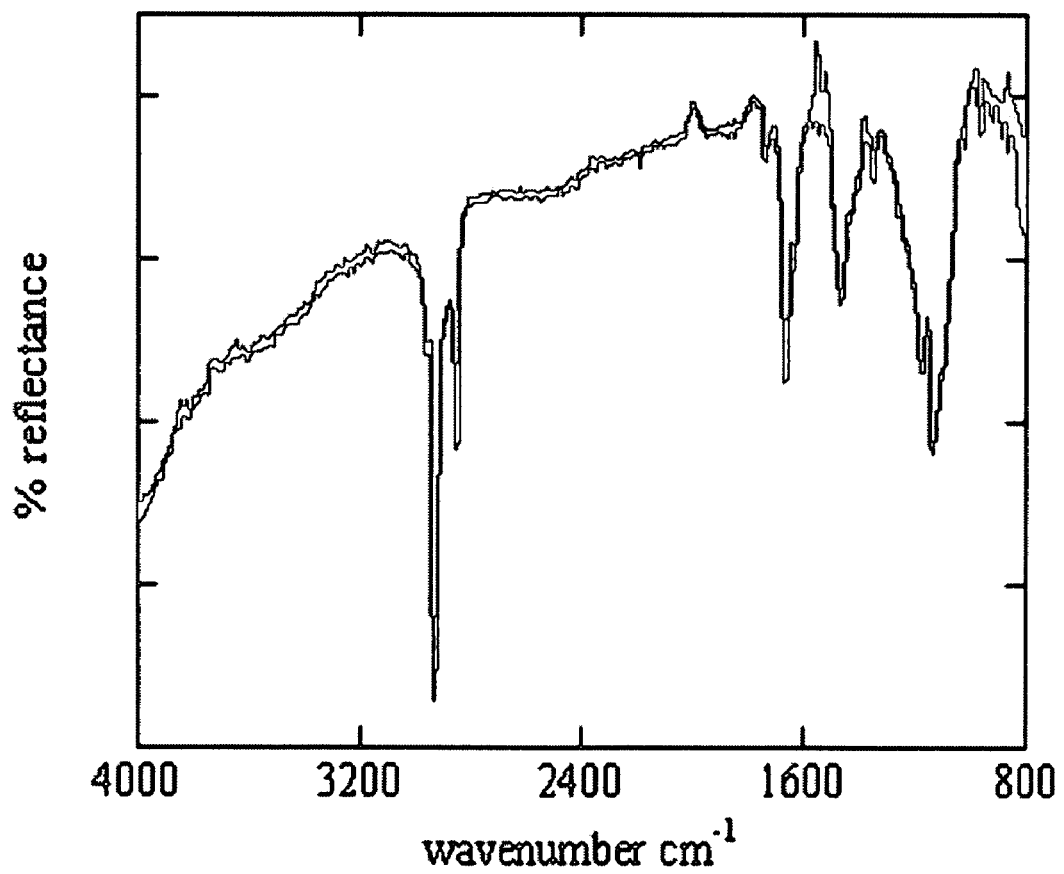
FIG. 12, depicts grazing angle FT-IR results for SAM of Example 2.

Formation of a monolayer on gold was monitored by contact angle, ellipsometry and FT-IR. Contact angle showed the formation of a slightly hydrophobic layer (48±2°), and ellipsometry demonstrates the formation of a single layer on the surface (layer thickness: 2.2±0.3 nm). The best evidence of deposition of the compound on gold comes from grazing angle FT-IR results (FIG. 12), with an absorption peak at 1666 cm$^{-1}$ corresponding to the carbonyl group of the amide bonds [18], and a peak at 1130 cm$^{-1}$ corresponding to the C—O bonds. Other significant bands in the IR spectra are the methylene vibrations of the alkyl chain at 2856 and 2927 cm$^{-1}$.

D. Cyclic Voltammetry Results

The analysis of the surfaces formed in this example; was carried out following previously reported procedures, such as discussed in Duevel, R. V.; Corn, R. M. *Anal. Chem.* 64, 337-342 (1992); Flink, S.; Boukamp, B. A.; van den Berg, A.; van Veggel, F. C. J. M.; Reinhoudt, D. N. *Journal of the American Chemical Society,* 120, 4652-4657 (1998); Flink, S.; Van Veggel, F. C. J. M.; Reinhoudt, D. N. *J. Phys. Chem. B.,* 103, 6515-6520 (1999); and Flink, S.; van Veggel, F. C. J. M.; Reinhoudt, D. N. *Adv. Mater.,* 12, 1315-1328 (2000); all of which are incorporated herein by reference in their entirety.

Cyclic voltammetry in the presence of potassium ferricyanide and potassium chloride showed the formation of a SAM that is insulating to the ferricyanide redox probe. In addition, this experiment showed that the sensor does not bind K$^+$ to a significant extent. Thus, a positively charged SAM, e.g., one with complexed potassium or other ions on the surface, does not block the redox process of a negatively charged species in solution such as ferricyanide because of electrostatic attraction between the SAM and the species in solution. The charged SAM acts as an ion-gate for the diffusion of electrolyte through the monolayer.

Cyclic voltammetry was used to determine the selectivity of the sensor using another redox probe, hexaammine ruthenium (III) chloride. This probe was selected based on previous CV studies of sensors that demonstrate that SAMs do not block the redox process of Ru(III), but a SAM with a layer of positive ions complexed with the sensor moiety of the monolayer effectively blocks the redox process of Ru(III). The presence of positively charged ions on the surface leads to blocking of the redox process because of electrostatic repulsion between the positively charged SAM and the positively charged ruthenium species.

Figure 13:
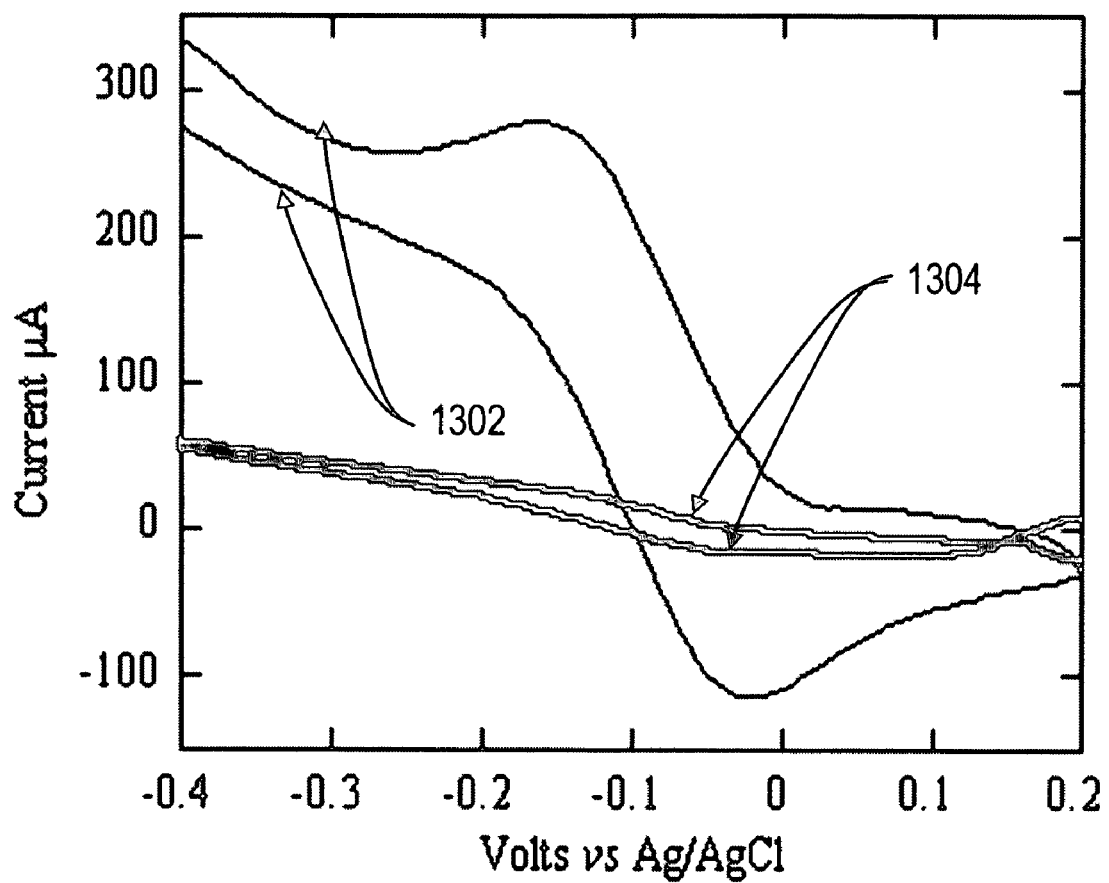
FIG. 13 depicts CV results obtained with hexaammine ruthenium (III) chloride for a surface in Example 2.

FIG. 13 shows the CV results obtained with hexaammine ruthenium (III) chloride at without lithium ions 1302 and in the presence of a 0.25 mM lithium ion solution 1304. The plot of FIG. 13 has been smoothed to remove switching transients.

The experiments were initially carried out with an aqueous solution of 1 mM Ru(NH$_3$)$_6$Cl$_3$ and 0.1 M tetrabutyl ammonium bromide. The film does not block the redox process with this solution. Titration experiments were subsequently conducted by adding aliquots of a solution containing 1 mM Ru(NH$_3$)$_6$Cl$_3$ and 0.1 M of a metal chloride or bromide. The experiments were thus are carried out with a constant concentration of the redox species and a total 0.1 M concentration of supporting electrolyte, thus eliminating ionic strength effects. The CVs did not change with the addition of potassium, sodium or ammonium salts.

FIG. 13 shows the CV after addition of 25 mM LiCl 1304. At this or higher concentration values the monolayer becomes insulating to the redox process of Ru(NH$_3$)$_6$Cl$_3$. Several experiments were carried out to obtain more quantitative results that would give a plot of redox current peak as a function of ion concentration, however, the insulating/conducting effect in the presence of Li$^+$ ions did not occur as a gradual decrease in conductivity but rather a one-step change in conductivity at a specific concentration value (about 25 mM), it is believed that this concentration value corresponds to that at which saturation of Li$^+$ ions on this SAM occurred. This phenomenon may also be related to diffusion of electrolyte through defects on the SAM. A quantitative analysis was also performed using impedance techniques to show the ability of the SAM to bind Li$^+$ ions selectively.

E. Impedance Spectroscopy Results

Figure 14:
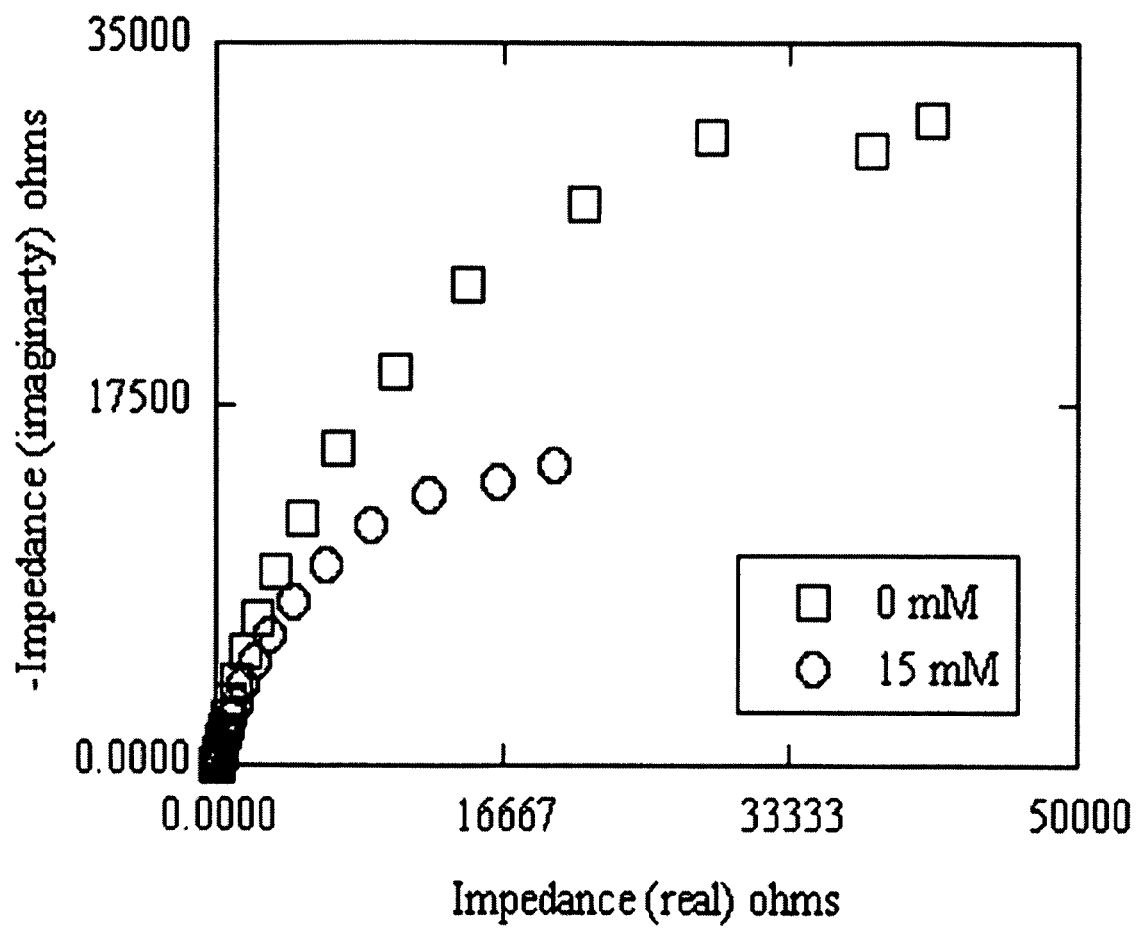
FIG. 14 depicts Nyquist plots of Example 2 obtained at −0.5 V vs Ag/AgCl with a supporting electrolyte solution of (1) 0 mM LiCl and 0.1 M tetrabutyl ammonium bromide (data points indicated by open squares) and (2) 15 mM LiCl and 0.085 M tetrabutyl ammonium bromide (data points indicated by open circles).

Experiments in the presence of a background electrolyte solution of 0.1 M tetraethylammonium chloride at −0.5 V vs Ag/AgCl and different concentrations of Li$^+$, K$^+$ or Na$^+$ were conducted. At the applied potential, the experimental Nyquist plots can be modeled using a Randles circuit. The circuit consists of a capacitance in parallel with the monolayer resistance and the Warburg impedance and the solution resistance in series with these components. The Warburg impedance accounts for diffusion processes at low frequencies. The effect of ion-complexation should result in changes in the monolayer capacitance, similar to changes in capacitance observed for multilayered films containing metal ions previously discussed. FIG. 14 illustrates Nyquist plots obtained at two different concentrations of $Li^+$ ions. The open squares represent data taken obtained with a supporting electrolyte solution of 0 mM LiCl and 0.1 M tetrabutyl ammonium bromide; and the open circles are for a supporting electrolyte solution of 15 mM LiCl and 0.085 M tetrabutyl ammonium bromide. From these Nyquist plots it was possible to obtain capacitance values for the monolayer that are related to ion concentration in solution.

Figure 15:
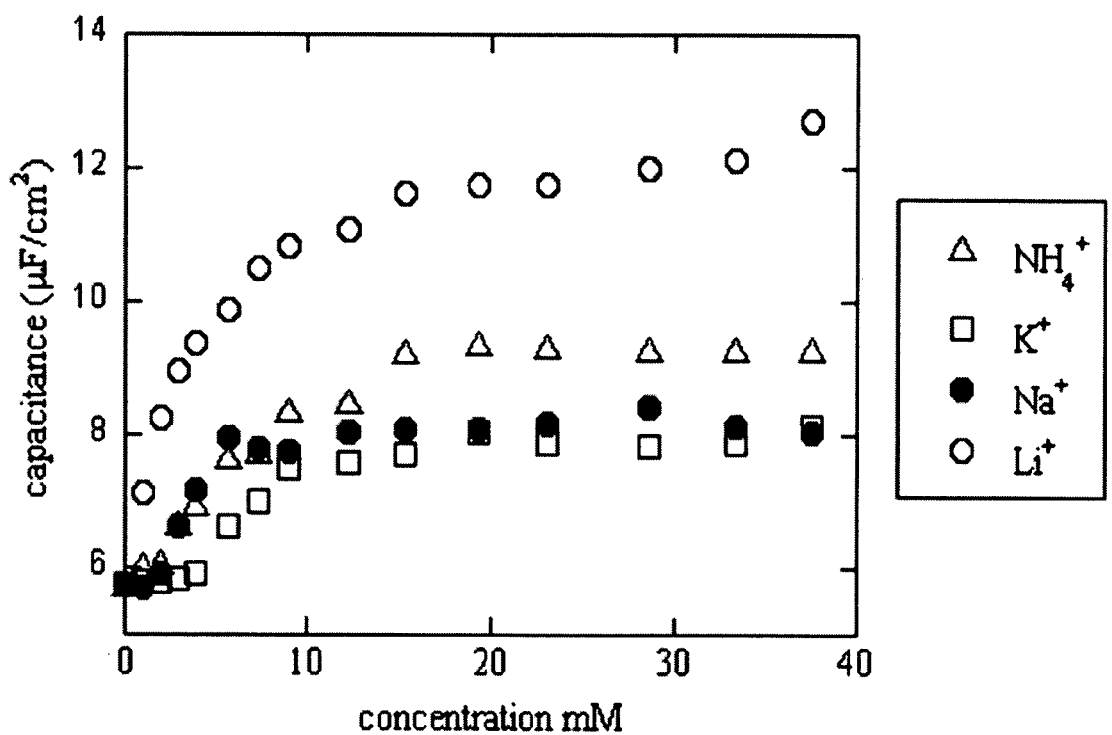
FIG. 15 depicts a plot of capacitance as a function of ion concentration for different ions in Example 2.

FIG. 15 shows a plot of capacitance changes vs ion concentration. The results indicate that the SAMs have a lower affinity for $Na^+$ and $NH^+$. $NH_4^+$ complexation was studied to provide evidence that the supporting electrolyte (tetrabutyl ammonium bromide or tetraethyl ammonium chloride) does not significantly interfere in the impedance measurements. FIG. 15 also demonstrates that the SAMs of this sensor molecule have selectivity for Li ions over potassium and sodium ions, with $\log K_{Li+,Na+} \sim -1.30$ and $\log K_{Li+,K+} \sim -0.92$. Selectivity was calculated by a method used in ion selective electrode applications, such as described, for example in: Benco, J. S.; Nienaber, H. A.; McGimpsey, W. G. *Anal. Chem.* 75, 152-156 (2003); and Bakker, E.; Buehlmann, P.; Pretsch, E. *Chem. Rev.*, 97, 3083-3132 (1997); both of which are incorporated herein by reference in their entirety.

Selectivity is represented as a logarithmic value and can be calculated using equation 1.

$$\log K_{i,j} = \log ([i]/[j]) \quad (1)$$

Here, [j] represents the concentration of the interfering ion in the plateau region of the plot, where the concentration of the interfering ion provides the maximum capacitance response. The concentration of the primary ion, [i], is the concentration that gives the same response as the maximum capacitance produce by the interfering ion, representing a minimum unambiguous detection limit for the primary ion.

F. Selectivity of Ionopore/Fluorophore

The ionophore of this example was also modified to contain a fluorophore that transduces the binding of ions via enhanced fluorescence emission. The modified ionophore portion is schematically depicted in FIG. 11B. In this modified compound, the ion binding site is essentially the same as in the ionophore. When measured in solution, selectivity values for the modified compound were $\log K_{Li+,Na+} \sim -3.36$, $\log K_{Li+,K+} \sim -1.77$.

G. Storage

The response of the analyte sensor of this example is not expected to change if stored in a cool dark environment.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. An analyte sensor comprising:
a substrate having a surface;
an electrically conductive material covering at least a portion of the surface;
an analyte sensor layer covering at least a portion of the electrically conductive material; the analyte sensor layer comprising analyte sensing molecules, the analyte sensing molecule comprising:
an analyte binding portion for a first signal of at least two signal transduction mechanisms, said analyte binding portion comprising an aza crown calixarene;
a fluorophore portion for a second signal of the at least two signal transduction mechanisms; and
a linker portion connecting the analyte sensing molecule to the electrically conductive material.

2. The analyte sensor of claim 1, wherein the analyte sensor layer is a substantially monolayer thick film.

3. The analyte sensor of claim 1, wherein the substrate comprises a material substantially transparent to one or more of an excitation wavelength and a fluorescence wavelength of the fluorophore portion.

4. The analyte sensor of claim 1, wherein the substrate comprises a silicon dioxide glass material.

5. The analyte sensor of claim 1, wherein the electrically conductive material comprises a material substantially transparent to one or more of an excitation wavelength and a fluorescence wavelength of the fluorophore portion.

6. The analyte sensor of claim 1, wherein the electrically conductive material comprises an electrically conductive oxide layer.

7. The analyte sensor of claim 1, wherein the electrically conductive material comprises one or more of indium tin oxide, tin oxide, fluorine-doped tin oxide, tin oxide, and zinc oxide.

8. The analyte sensor of claim 1, wherein the analyte binding portion is an ionophore.

9. The analyte sensor of claim 8, wherein the ionophore is an ionophore for a monovalent cation selected from the group consisting of: lithium, sodium, potassium and cesium ions.

10. The analyte sensor of claim 1, wherein the fluorophore portion comprises anthracene.

11. The analyte sensor of claim 1, wherein the linker portion comprises a $C_1$-$C_{20}$ alkyl group.

12. The analyte sensor of claim 1, wherein the first signal comprises an electrochemical signal.

13. The analyte sensor of claim 12, wherein the electrochemical signal comprises impedance or capacitance measurement.

14. The analyte sensor of claim 1, wherein the second signal comprises an optical signal.

15. An microfluidic device comprising:
a substrate having a surface;
an electrically conductive material covering at least a portion of the surface;
an analyte sensor layer covering at least a portion of the electrically conductive material; the analyte sensor layer comprising a substantially monolayer thick film of an analyte sensing molecule, the analyte sensing molecule comprising:

an analyte binding portion for a first signal of at least two signal transduction mechanisms, said analyte binding portion comprising an aza crown calixarene;

a fluorophore portion for a second signal of the at least two signal transduction mechanisms; and a linker portion connecting the analyte sensing molecule to the electrically conductive material;

a reference electrode in electrical contact with the analyte sensor layer; and a counter electrode in electrical contact with the analyte sensor layer.

16. The microfluidic device of claim 15, wherein the linker portion comprises a $C_1$-$C_{20}$ alkyl group.

* * * * *